US011485768B2

(12) United States Patent
Vander Elst

(10) Patent No.: US 11,485,768 B2
(45) Date of Patent: Nov. 1, 2022

(54) IMMUNOGENIC CD1D BINDING PEPTIDES

(71) Applicant: IMCYSE SA, Liège (BE)

(72) Inventor: Luc Vander Elst, Obaix (BE)

(73) Assignee: IMCYSE SA, Liège (BE)

( * ) Notice: Subject to any disclaimer, the term of this patent is extended or adjusted under 35 U.S.C. 154(b) by 213 days.

(21) Appl. No.: 16/091,549

(22) PCT Filed: Apr. 19, 2017

(86) PCT No.: PCT/EP2017/059302
§ 371 (c)(1),
(2) Date: Oct. 5, 2018

(87) PCT Pub. No.: WO2017/182528
PCT Pub. Date: Oct. 26, 2017

(65) Prior Publication Data
US 2019/0106477 A1    Apr. 11, 2019

(30) Foreign Application Priority Data

Apr. 19, 2016 (EP) .................................. 16166054

(51) Int. Cl.
| C07K 14/74 | (2006.01) |
| A61K 39/00 | (2006.01) |
| A61P 37/02 | (2006.01) |
| A61P 37/08 | (2006.01) |
| A61P 37/06 | (2006.01) |
| A61P 35/00 | (2006.01) |

(52) U.S. Cl.
CPC ........ C07K 14/70539 (2013.01); A61K 39/00 (2013.01); A61K 39/0008 (2013.01); A61P 35/00 (2018.01); A61P 37/02 (2018.01); A61P 37/06 (2018.01); A61P 37/08 (2018.01); A61K 2039/5158 (2013.01); A61K 2039/55505 (2013.01)

(58) Field of Classification Search
None
See application file for complete search history.

(56) References Cited

U.S. PATENT DOCUMENTS

| 4,599,231 A | 7/1986 | Milich et al. |
| 4,886,782 A | 12/1989 | Good et al. |
| 5,433,948 A | 7/1995 | Thomas et al. |
| 5,552,142 A | 9/1996 | Thomas et al. |
| 5,589,175 A | 12/1996 | Vahlne et al. |
| 5,633,234 A | 5/1997 | August et al. |
| 5,770,202 A | 6/1998 | Thomas et al. |
| 5,773,002 A | 6/1998 | Thomas et al. |
| 5,863,528 A | 1/1999 | Hawley et al. |
| 6,399,383 B1 | 6/2002 | Apt et al. |
| 6,602,509 B1 | 8/2003 | Saint-Remy et al. |
| 6,656,471 B1 | 12/2003 | Sastry et al. |
| 6,759,046 B1 | 7/2004 | Gaudernack et al. |
| 7,157,089 B1 | 1/2007 | Mizzen et al. |
| 7,306,804 B2 | 12/2007 | Sastry et al. |
| 8,999,346 B2 | 4/2015 | Saint-Remy |
| 9,044,507 B2 | 6/2015 | Saint-Remy |
| 9,248,171 B2 | 2/2016 | Saint-Remy |
| 9,249,202 B2 | 2/2016 | Saint-Remy |
| 9,394,517 B2 | 7/2016 | Saint-Remy |
| 9,861,661 B2 | 1/2018 | Saint-Remy |
| 10,023,847 B2* | 7/2018 | Saint-Remy ............ A61P 31/00 |
| 2003/0049723 A1 | 3/2003 | Zhang et al. |
| 2003/0104570 A1 | 6/2003 | Cabezon Silva et al. |
| 2003/0129205 A1 | 7/2003 | Saint-Remy et al. |
| 2003/0152581 A1 | 8/2003 | Saint-Remy et al. |
| 2004/0077045 A1 | 4/2004 | Zhang et al. |
| 2005/0032039 A1 | 2/2005 | Sastry et al. |
| 2005/0107256 A1 | 5/2005 | Barnwell et al. |
| 2005/0181446 A1 | 8/2005 | Roggen |
| 2005/0196386 A1 | 9/2005 | Blazar et al. |
| 2005/0202044 A1 | 9/2005 | Mizzen et al. |
| 2006/0182763 A1 | 8/2006 | Kim et al. |
| 2006/0211091 A1 | 9/2006 | Zhang et al. |
| 2006/0216301 A1 | 9/2006 | Tahara et al. |
| 2006/0269561 A1 | 11/2006 | Paterson et al. |

(Continued)

FOREIGN PATENT DOCUMENTS

| JP | 2004147649 A | 5/2004 |
| JP | 2010500308 A | 1/2010 |

(Continued)

OTHER PUBLICATIONS

Teng, Shaolei et al. "Structural assessment of the effects of amino acid substitutions on protein stability and protein protein interaction." International journal of computational biology and drug design vol. 3,4 (2010): 334-49. doi:10.1504/IJCBDD.2010.038396 (Year: 2010).*
Castano, A. Raul, et al. "Peptide binding and presentation by mouse CD1." Science 269.5221 (1995): 223-226. (Year: 1995).*
Nishioka, Yusuke, et al. "CD1d-restricted type II NKT cells reactive with endogenous hydrophobic peptides." Frontiers in immunology 9 (2018): 548. (Year: 2018).*
Girardi, Enrico, Jing Wang, and Dirk M. Zajonc. "Structure of an α-helical peptide and lipopeptide bound to the nonclassical major histocompatibility complex (MHC) class I molecule CD1d." Journal of Biological Chemistry 291.20 (2016): 10677-10683. (Year: 2016).*

(Continued)

*Primary Examiner* — Michael Szperka
*Assistant Examiner* — Lia E Taylor
(74) *Attorney, Agent, or Firm* — Nixon & Vanderhye, PC

(57) ABSTRACT

The invention relates to isolated immunogenic peptides comprising a CD1d binding peptide, and immediately adjacent or separated from said CD1d binding peptide, a redox motif sequence which is further flanked by a histidine or tryptophan amino acids. The invention further relates to these peptides for use as a medicament The invention further relates to methods wherein these peptides are used for generating NKT cells which are cytolytic against cells presenting the cognate antigen.

19 Claims, No Drawings

Specification includes a Sequence Listing.

(56) References Cited

U.S. PATENT DOCUMENTS

| | | |
|---|---|---|
| 2007/0160620 A1 | 7/2007 | Mizzen et al. |
| 2007/0184023 A1 | 8/2007 | Rasmussen et al. |
| 2008/0176247 A1 | 7/2008 | Chou et al. |
| 2009/0012004 A1 | 1/2009 | Sette et al. |
| 2010/0068193 A1 | 3/2010 | Brunsvig et al. |
| 2010/0183652 A1 | 7/2010 | Page et al. |
| 2010/0203083 A1 | 8/2010 | Lux et al. |
| 2010/0033088 A1 | 12/2010 | Saint Remy |
| 2010/0303866 A1 | 12/2010 | Saint-Remy |
| 2010/0330088 A1 | 12/2010 | Saint-Remy |
| 2011/0002903 A1 | 1/2011 | Saint-Remy |
| 2011/0110964 A1 | 5/2011 | Saint-Remy |
| 2011/0111395 A1 | 5/2011 | Saint-Remy |
| 2011/0111502 A1 | 5/2011 | Saint Remy |
| 2012/0009678 A1 | 1/2012 | Saint-Remy |
| 2012/0009685 A1* | 1/2012 | Kim .................. C07K 14/4711 436/86 |
| 2013/0095133 A1 | 4/2013 | Klatzmann et al. |
| 2013/0259885 A1 | 10/2013 | Saint-Remy |
| 2014/0370044 A1 | 12/2014 | Saint-Remy |
| 2014/0377299 A1 | 12/2014 | Saint-Remy |
| 2015/0110821 A1 | 4/2015 | Saint-Remy |
| 2015/0209446 A1* | 7/2015 | Santamaria .......... A61K 47/646 424/491 |
| 2015/0216901 A1 | 8/2015 | Saint Remy |
| 2016/0091492 A1 | 3/2016 | Saint-Remy |
| 2016/0108103 A1 | 4/2016 | Saint-Remy |
| 2016/0194367 A1 | 7/2016 | Saint-Remy |
| 2016/0250255 A1 | 9/2016 | Saint-Remy |
| 2016/0339121 A1 | 11/2016 | Saint-Remy |
| 2017/0100466 A1 | 4/2017 | Saint-Remy |
| 2018/0228912 A1* | 8/2018 | Saint-Remy ..... C07K 14/70539 |
| 2018/0258154 A1 | 9/2018 | Saint-Remy |
| 2018/0346887 A1 | 12/2018 | Saint-Remy |

FOREIGN PATENT DOCUMENTS

| | | | |
|---|---|---|---|
| WO | WO-8504103 A1 | 9/1985 | |
| WO | WO-9205800 A1 | 4/1992 | |
| WO | WO-9308279 A1 | 4/1993 | |
| WO | WO-9405790 A1 | 3/1994 | |
| WO | WO-9740852 A1 | 11/1997 | |
| WO | WO-9958552 A2 | 11/1999 | |
| WO | WO-0029008 A2 | 5/2000 | |
| WO | WO-0170263 A1 | 9/2001 | |
| WO | WO-0200892 A1 | 1/2002 | |
| WO | WO-02095051 A2 | 11/2002 | |
| WO | WO-02097070 A1 | 12/2002 | |
| WO | WO-03072731 A2 | 9/2003 | |
| WO | WO-2004018667 A1 | 3/2004 | |
| WO | WO-2004024766 A1 | 3/2004 | |
| WO | WO-2004030616 A2 * | 4/2004 | ............. C07H 21/04 |
| WO | WO-2005012502 A2 | 2/2005 | |
| WO | 2005042575 A2 | 5/2005 | |
| WO | WO-2005039613 A1 | 5/2005 | |
| WO | WO-2005042575 A2 | 5/2005 | |
| WO | WO-2005086781 A2 | 9/2005 | |
| WO | WO-2006059529 A1 | 6/2006 | |
| WO | WO-2007104715 A2 | 9/2007 | |
| WO | WO-2007135684 A2 | 11/2007 | |
| WO | 2008017517 A1 | 2/2008 | |
| WO | WO-2009042215 A3 | 4/2009 | |
| WO | 2009101204 A2 | 8/2009 | |
| WO | 2009101205 A2 | 8/2009 | |
| WO | 2009101206 A2 | 8/2009 | |
| WO | 2009101208 A2 | 8/2009 | |
| WO | WO-2009100505 A1 | 8/2009 | |
| WO | WO-2009101204 A2 | 8/2009 | |
| WO | WO-2009101207 A1 | 8/2009 | |
| WO | WO-2009106073 A2 | 9/2009 | |
| WO | WO-2010037395 A2 | 4/2010 | |
| WO | 2012069568 A2 | 5/2012 | |
| WO | 2013121296 A1 | 8/2013 | |
| WO | WO-2013113076 A1 | 8/2013 | |
| WO | 2015063176 A1 | 5/2015 | |
| WO | WO-2015063176 A1 | 5/2015 | |
| WO | 2016059236 A1 | 4/2016 | |
| WO | 2016059236 A2 | 4/2016 | |
| WO | WO-2016059236 A1 | 4/2016 | |

OTHER PUBLICATIONS

Beynon-Jones, Siân M., Antony N. Antoniou, and Simon J. Powis. "Mutational analysis of the oxidoreductase ERp57 reveals the importance of the two central residues in the redox motif." FEBS letters 580.7 (2006): 1897-1902. (Year: 2006).*

Reddy Chichili, Vishnu Priyanka et al. "Linkers in the structural biology of protein-protein interactions." Protein science : a publication of the Protein Society vol. 22,2 (2013): 153-67. doi:10.1002/pro.2206 (Year: 2013).*

Tam, James P., Jiaxi Xu, and Khee Dong Eom. "Methods and strategies of peptide ligation." Peptide Science: Original Research on Biomolecules 60.3 (2001): 194-205. (Year: 2001).*

Chandrudu S, Simerska P, Toth I. Chemical methods for peptide and protein production. Molecules. 2013;18(4):4373-4388. Published Apr. 12, 2013. doi:10.3390/molecules18044373 (Year: 2013).*

Zhang D et al., "Preclinical experimental models of drug metabolism and disposition in drug discovery and development," Acta Pharmaceutica Sinica B 2012;2(6):549-561.

De Groot A et al., "Immunogenicity of protein therapeutics," Trends in Immunology, vol. 28, No. 11, 482-490, 2007.

Final Office Action dated Jan. 20, 2012 issued in U.S. Appl. No. 12/377,048, filed Feb. 10, 2009, related application.

Final Office Action dated Aug. 9, 2012 issued in U.S. Appl. No. 12/377,048, filed Feb. 10, 2009, related application.

Non-Final Office Action dated Apr. 20, 2015 issued in U.S. Appl. No. 12/377,048, filed Feb. 10, 2009, related application.

Notice of Allowance dated Sep. 22, 2015 issued in U.S. Appl. No. 12/377,048, filed Feb. 10, 2009, related application.

Non-Final Office Action dated Feb. 20, 2018 issued in U.S. Appl. No. 14/976,259, filed Dec. 21, 2015, related application.

Final Office Action dated Oct. 26, 2018 issued in U.S. Appl. No. 14/976,259, filed Dec. 21, 2015, related application.

Advisory Action dated Feb. 4, 2019 issued in U.S. Appl. No. 14/976,259, filed Dec. 21, 2015, related application.

Non-Final Office Action dated May 17, 2019 issued in U.S. Appl. No. 14/976,259, filed Dec. 21, 2015, related application.

Non-Final Office Action dated May 20, 2014 issued in U.S. Appl. No. 12/735,744, filed Aug. 13, 2010, related application.

Final Office Action dated Jun. 5, 2015 issued in U.S. Appl. No. 12/735,744, filed Aug. 13, 2010, related application.

Notice of Allowance dated Sep. 28, 2015 issued in U.S. Appl. No. 12/735,744, filed Aug. 13, 2010, related application.

Non-Final Office Action dated Jan. 9, 2014 issued in U.S. Appl. No. 12/735,744, filed Aug. 13, 2010, related application.

Non-Final Office Action dated Nov. 25, 2014 issued in U.S. Appl. No. 12/735,744, filed Aug. 13, 2010, related application.

Non-Final Office Action dated Dec. 1, 2017 issued in U.S. Appl. No. 14/980,832, filed Dec. 28, 2015 related application.

Non-Final Office Action dated Sep. 11, 2018 issued in U.S. Appl. No. 14/980,832, filed Dec. 28, 2015 related application.

Final Office Action dated Jan. 8, 2019 issued in U.S. Appl. No. 14/980,832, filed Dec. 28, 2015 related application.

Notice of Allowance dated Apr. 3, 2019 issued in U.S. Appl. No. 14/980,832, filed Dec. 28, 2015 related application.

Non-Final Office Action dated Jul. 11, 2013 issued in U.S. Appl. No. 12/735,739, filed Aug. 13, 2010 related application.

Final Office Action dated Feb. 20, 2014 issued in U.S. Appl. No. 12/735,739, filed Aug. 13, 2010 related application.

Non-Final Office Action dated Jan. 11, 2016 issued in U.S. Appl. No. 12/735,739, filed Aug. 13, 2010 related application.

Final Office Action dated Aug. 31, 2016 issued in U.S. Appl. No. 12/735,739, filed Aug. 13, 2010 related application.

Non-Final Office Action dated Oct. 2, 2018 issued in U.S. Appl. No. 15/388,398, filed Dec. 22, 2016 related application.

(56) References Cited

OTHER PUBLICATIONS

Final Office Action dated Apr. 15, 2019 issued in U.S. Appl. No. 15/388,398, filed Dec. 22, 2016 related application.
Non-Final Office Action dated Jan. 22, 2013 issued in U.S. Appl. No. 12/735,740, filed Aug. 13, 2010 related application.
Final Office Action dated Jul. 10, 2013 issued in U.S. Appl. No. 12/735,740, filed Aug. 13, 2010 related application.
Non-Final Office Action dated Apr. 1, 2014 issued in U.S. Appl. No. 12/735,740, filed Aug. 13, 2010 related application.
Notice of Allowance dated Oct. 2, 2014 issued in U.S. Appl. No. 12/735,740, filed Aug. 13, 2010 related application.
Notice of Allowability dated Mar. 3, 2015 issued in U.S. Appl. No. 12/735,740, filed Aug. 13, 2010 related application.
Advisory Action dated Mar. 20, 2017 issued in U.S. Appl. No. 14/589,134, filed Jan. 5, 2015 related application.
Final Office Action dated Jan. 19, 2018 issued in U.S. Appl. No. 14/589,134, filed Jan. 5, 2015 related application.
Final Office Action dated Dec. 2, 2016 issued in U.S. Appl. No. 14/589,134, filed Jan. 5, 2015 related application.
Notice of Allowance dated Feb. 21, 2019 issued in U.S. Appl. No. 14/589,134, filed Jan. 5, 2015 related application.
Non-Final Office Action dated Jul. 14, 2017 issued in U.S. Appl. No. 14/589,134, filed Jan. 5, 2015 related application.
Non-Final Office Action dated Aug. 17, 2016 issued in U.S. Appl. No. 14/589,134, filed Jan. 5, 2015 related application.
Non-Final Office Action dated Oct. 5, 2018 issued in U.S. Appl. No. 14/589,134, filed Jan. 5, 2015 related application.
Non-Final Office Action dated Jan. 18, 2013 issued in U.S. Appl. No. 12/735,742, filed Aug. 13, 2010 related application.
Non-Final Office Action dated Aug. 24, 2017 issued in U.S. Appl. No. 14/450,722, filed Aug. 4, 2014 related application.
Final Office Action dated Dec. 28, 2017 issued in U.S. Appl. No. 14/450,722, filed Aug. 4, 2014 related application.
Advisory Action dated May 9, 2018 issued in U.S. Appl. No. 14/450,722, filed Aug. 4, 2014 related application.
Non-Final Office Action dated Jan. 14, 2019 issued in U.S. Appl. No. 14/450,722, filed Aug. 4, 2014 related application.
Non-Final Office Action dated Jun. 17, 2016 issued in U.S. Appl. No. 13/988,925, filed Jun. 6, 2013 related application.
Final Office Action dated Dec. 28, 2016 issued in U.S. Appl. No. 13/988,925, filed Jun. 6, 2013 related application.
Non-Final Office Action dated Nov. 9, 2017 issued in U.S. Appl. No. 13/988,925, filed Jun. 6, 2013 related application.
Notice of Allowance dated Mar. 26, 2018 issued in U.S. Appl. No. 13/988,925, filed Jun. 6, 2013 related application.
Non-Final Office Action dated Feb. 23, 2017 issued in U.S. Appl. No. 14/375,324, filed Jul. 29, 2014 related application.
Final Office Action dated Oct. 30, 2017 issued in U.S. Appl. No. 14/375,324, filed Jul. 29, 2014 related application.
Non-Final Office Action dated Jun. 25, 2018 issued in U.S. Appl. No. 14/375,324, filed Jul. 29, 2014 related application.
Final Office Action dated Mar. 25, 2019 issued in U.S. Appl. No. 14/375,324, filed Jul. 29, 2014 related application.
Non-Final Office Action dated Sep. 7, 2018 issued in U.S. Appl. No. 14/894,221, filed Nov. 25, 2015 related application.
Notice of Allowance dated Apr. 15, 2019 issued in U.S. Appl. No. 14/894,221, filed Nov. 25, 2015 related application.
Non-Final Office Action dated Sep. 18, 2018 issued in U.S. Appl. No. 15/516,045, filed Mar. 31, 2017 related application.
Final Office Action dated Feb. 13, 2019 issued in U.S. Appl. No. 15/516,045, filed Mar. 31, 2017 related application.
Non-Final Office Action dated Jun. 8, 2018 issued in U.S. Appl. No. 15/151,868, filed May 11, 2016 related application.
Final Office Action dated Mar. 19, 2019 issued in U.S. Appl. No. 15/151,868, filed May 11, 2016 related application.
Garcin, E.B., et al., "Structural and Mechanistic Insights into Unusual Thiol Disulfide Oxidoreductase," The Journal of Biological Chemistry, vol. 287, No. 3 pp. 1688-1697, Jan. 13, 2012.

Matsuda J L et al., "CD1d-restricted iNKT cells, the 'Swiss-Army Knife' of the immune system," Current Opinion in Immunology, vol. 20, No. 3, Jun. 1, 2008, pp. 358-368.
Fomenko D E et al., "Identity and functions of CxxC-derived motifs," Biochemistry, vol. 42, No. 38, Sep. 30, 2003, pp. 11214-11225.
Non-Final Office Action issued in co-pending U.S. Appl. No. 15/761,223, dated Apr. 22, 2021.
Final Office Action issued in co-pending U.S. Appl. No. 15/761,223, dated Nov. 29, 2021.
Pipe et al., "New high-technology products for the treatment of haemophilia" Haemophilia 10 (Suppl. 4), 55-63 (2004).
PCT International Search Report and Written Opinion dated May 4, 2018 in connection with PCT International Patent Application No. PCT/EP2018/055501.
European Summons to attend oral proceedings pursuant to Rule 115(1) EPC in connection with European Patent Application No. 13709300.1, Dec. 21, 2018.
Davis M M et al., "Interrogating the repertoire: broadening the scope of peptide-MHC multimer analysis," Nature Reviews, Immunology, Aug. 2011, vol. 11, 551-558.
PCT International Search Report and Written Opinion dated Jun. 26, 2017 for PCT International Patent Application No. PCT/EP2017/059302, 11 pages.
Database Geneseq (online), Jan. 26, 2017 "Human preproinsulin (PPI) antigenic peptide, Seq Id 164," XP002770300, retrieved from EBI accession No. GSP:BDK51134.
Abrahimians E M et al., "Thioreductase-Containing Epitopes Inhibit the Development of Type 1 Diabetes in the NOD Model," Frontiers in Immunology, vol. 7, Mar. 2, 2016, XP055371835.
Chapter III Immune Molecules.
Pillai A B et al., "Host NKT Cells Can Prevent Graft-versus-Host Disease and Permit Graft Antitumor Activity after Bone Marrow Transplantation," The Journal of Immunology, 2007, 178: 6242-6251.
Hemmer B et al., "Minimal peptide length requirements for CD4+ T cell clones—implications for molecular mimicry and T cell survival," International Immunology, vol. 12, No. 3, pp. 375-383, 2000.
Vignali D A A et al., "Amino Acid Residues that Flank Core Peptide Epitopes and the Extracellular Domains of CD4 Modulate Differential Signaling through the T Cell Receptor," J. Exp. Med., vol. 179, Jun. 1994, 1945-1956.
Lovitch S B et al., "Amino-Terminal Flanking Residues Determine the Conformation of a Peptide-Class II MBC Complex," J Immunol 2006; 176:2958-2968.
Japanese Final Decision for Rejection in connection with Japanese Patent Application No. 2016-516134.
Abrahimians et al., "MHC class II-restricted epitopes containing an oxidoreductase activity prompt CD4+ T cells with apoptosis-inducing properties," Frontiers in Immunology, vol. 6, 2 (2015), pp. 1-5.
Aleksza et al., "Altered cytokine expression of peripheral blood lymphocytes in polymyositis and dermatomyositis," (2005) Ann. Rheum. Dis. 64, 1485-1489.
Aley & Gillin, "Giardia lambiia: post-translational processing and status of exposed cysteine residues in TSA 417, a variable surface antigen" (1993) Exp Parasitol. 77, 295-305.
Apostolou et al., "Evidence for two subgroups of CD4−CD8− NKT cells with distinct TCR alpha beta repertoires and differential distribution in lymphoid tissues," J Immunol. 165(5):2481-90 (2000).
Appella et al., "Analysis of the structure of naturally processed peptides bound by class I and class II major histocompatibility complex molecules." EXS. (1995) 73:105-19.
Arunachalam et al., "Enzymatic reduction of disulfide bonds in lysosomes: Characterization of a Gamma-interferon-inducible lysosomal thiol reductase (GILT)," (2000) Proc. Natl. Acad. Sci USA, vol. 97, No. 2, 745-750.
Ascherio et al., "Environmental factors in multiple sclerosis," Expert Rev Neurother. 13(12S):3-9 (2013).
Azoury-Ziadeh et al., "T-Helper Epitopes Identified Within the E6 Transforming Protein of Cervical Cancer-Associated Human Papillomavirus Type 16," Viral Immunology, 1999, 12(4):297-312.

(56) References Cited

OTHER PUBLICATIONS

Balato et al., "Natural killer T cells: An unconventional T-cell subset with diverse effector and regulatory functions," Journal of Investigative Dermatology 129: 1628-1642 (2009).
Batten et al., "Immune response to stem cells and strategies to induce tolerance," (2007) Phil. Trans. R. Soc. B 362, 1343-1356.
Boisgerault et al., "Differential roles of direct and indirect allorecognition pathways in the rejection of skin and corneal transplants," (2009) Transplantation 87(1): 16-23.
Bolivar et al., "Molecular cloning of a zinc finger autoantigen transiently associated with interphase nucleolus and mitotic centromeres and midbodies. Orthologous proteins with nine CXXC motifs highly conserved form nematodes to humans," J. Biol, Chem., vol. 274, (1999), pp. 36456-36464.
Bower et al., "Two Members of the Thioredoxin-h Family Interact with the Kinase Domain of a *Brassica* S Locus Receptor Kinase," (1996) The plant cell, vol. 8, 1641-1650.
Braun et al., "Acute rejection in the absence of cognate recognition of allograft by T cells," J. Immunol., vol. 166, No. 8, (2001), pp. 4879-4883.
Brinks et al., "Immunogenicity of Therapeutic Proteins: The Use of Animal Models," Pharm Res (2011) 28:2379-2385.
Brinster et al., "Bone Marrow-Derived Dendritic Cells Reverse the Anergic State of CD4+CD25+ T Cells without Reversing Their Suppressive Function," (2005), The Journal of Immunology 175:7332-7340.
Brinster et al., "Costimulatory effects of IL-1 on the expansion/differentiation of CD4+CD25+Foxp3+and CD4+CD25+Foxp3--T cells," J. Leukoc. Biol., vol. 84, (2008), pp. 480-487.
Cao et al., "Prevention of gene transfer-induced inhibitor formation by nasal administration of human F.IX T cell epitope in a murine model of hemophilia B.," Blood, vol. 104(11), (2004), pp. 121A-122A.
Capon et al., "The CD4-gp120 Interaction and Aids Pathogenesis," (1991) Ann. Rev. Immunol 9, 649-678.
Caro-Aguilar et al., "Chimeric epitopes delivered by polymeric synthetic linear peptides induce I protective immunity to malaria," Microbes Infect. 7:1324-1337 (2005).
Carlier et al., "Increased Synapse Formation Obtained by T cell Epitopes Containing a CxxC Motif in Flanking Residues Convert CD4+ T Cells into Cytolytic Effectors," PLOS One, Oct. 2012, vol. 7, Issue 10, e45366, pp. 1-16.
Carlier et al., "Control of asthma by in vitro-induced allergen-specific regulatory T cells in the mouse," Munksgaard Allergy. 62(Suppl 83):555 (Abstract 1 616) (2007).
Castano et al., "Peptide binding and presentation by mouse CD1," Science 269: 223-226 (1995).
Cavone et al., "Long-term suppression of EAE relapses by pharmacological impairment of epitope spreading," Br J Pharmacol 171 (6):1501-9 (2014).
Celis et al., "Induction of anti-tumor cytotoxic T lymphocytes in normal humans using primary cultures and synthetic peptide epitopes," Proc Natl Acad Sci USA. Mar. 15, 1994;91 (6):2105-9.
Chen et al., "Induction of dominant transplantation tolerance by an altered peptide ligand of the male antigen Dby," (2004) J Clin. Invest. 113(12), 1754-1762.
Chen et al., "Glucocorticoid amplifies Il-2-dependent expansion of functional FoxP3+CD4+CD25+ T regulatory cells in vivo and enhances their capacity to suppress EAE," (2006) Eur. J. Immunol. 36, 2139-2149.
Chuanlin ed., Molecular Immunology, Fudan University Press, Shanghai Medical College Press; publication date: May 2001; pp. 428-429, 433-436 (English language translation provided) (15 pages).
Corthay et al., "CD4+ T Cells Cooperate with Macrophages for Specific Elimination of MHC Class II-Negative Cancer Cells," (2007) Adv Exp Med Biol. 590, 195-208.
Cotton et al., "Oxidative inhibition of human soluble catechol-O-methyltransferase," (2004) Biol. Chem. vol. 279: 23710-718.
Credo Reference, (2012).

Crellin et al., "Altered activation of AKT is required for the suppressive function of human CD4+CD25+ T regulatory cells," Blood 1 09(5):2014-2022 (2007).
Crompton et al., "Advances and challenges in malaria vaccine development," The Journal of Clinic Investigation, 2010, vol. 120, pp. 4168-4178.
Davids et al., A new family of giardial cysteine-rich non-VSP protein genes and a novel cyst protein, PLOS. One. vol. 1, (2006), e44.
Davis et al., "Interrogating the repertoire: broadening the scope of peptide-MHC multimer analysis," Nature Rev. Immunology, (2011), 11, 551-558.
De La Cruz et al., "The immunologic significance of variation within malaria circumsporozoite protein sequences," J. Immunol., vol. 142, (1989), pp. 3568-3575.
Desmetz et al., "Proteomics-Based Identification of HSP60 as a Tumor-Associated Antigen in Early Stage Breast Cancer and Ductal Carcinoma in situ," Journal of Proteome Research (2008), 7, 3830-3837.
Dobrzanski, "Expanding roles for CD4T cells and their subpopulations in tumor immunity and therapy," Frontiers in Oncology, Mar. 2013, vol. 3, Article 63, pp. 1-19.
Dobrzynski et al., "Prevention of cytotoxic T lymphocyte responses to factor IX-expressing hepatocytes by gene transfer-induced regulatory T cells," Proc. Natl. Acad. Sci. U.S.A., vol. 103, (2006), pp. 4592-4597.
Eberl et al., "Tissue-specific segregation of CD1d-dependent and CD1d-independent NK T cells," J. Immunol., vol. 162, (1999), pp. 6410-6419.
Facktor et al., "Hypersensitivity to tetanus toxoid," J Allergy Clin Immunol. Jul. 1973;52(1): 1-12.
Fan et al., "Co-immunization of BALB/c mice with recombinant immunogens containing G protein fragment and chimeric CTL epitope of respiratory syncytial virus induces enhanced cellular immunity and high level of antibody response," (2005) Vaccine 23, 4453-4461.
Fomenko et al., "Identity and functions of CxxC-derived motifs," Biochemistry, vol. 42, (2003), pp. 11214-11225.
Francois et al., "The CD4+ T-Cell Response of Melanoma Patients to a MAGE-A3 Peptide Vaccine Involves Potential Regulatory T Cells," Cancer Res. 69(10):4335-4345 (2009).
Frankel et al., "Characterization of diphtheria fusion proteins targeted to the human interleukin-3 receptor," Protein Eng. 13(8):575-81 (2000).
Freeman (Molecular Cell Biology, 4th Edition, Lodish et al., Eds, New York, 2000, section 6.3, "Viruses: Structure, Function, and Uses").
Ge et al., "An hsp 70 fusion protein vaccine potentiates the immune response against Japanese encephalitis virus," (2007) Arch. Viral 152, 125-135.
Geluk et al., "HLA-DR binding analysis of peptides from islet antigens in IDDM," Diabetes, vol. 47, (1998), pp. 1594-1601.
GenBank AA5961 0.1, 1995, p. 1.
GenBank AAA58655.1, 1994, p. 1.
GenBank FPAA051928, 1997, p. 1.
GenBank M77349.1—Skonier et al., "Human transforming growth factor-beta induced gene product (BIGH3) mRNA, complete cds," Jan. 14, 1995 (3 pages).
GenPept PDB 5GSB_A, 2017, pp. 1-2.
Gentile et al., "Thyroglobulin as an autoantigen: what can we learn about immunopathogenicity from the correlation of antigenic properties with protein structure?," (2004) Immunol 112 13-25.
Girardi et al., "Structure of an alpha-helical peptide and lipopeptide bound to the nonclassical major histocompatibility complex (MHC) class I molecule CD1 d," J Biol Chem. 291 (20):1 0677-83 (2016).
Gross et al., "Simple conditioning with monospecific CD4+CD25+ regulatory T cells for bone marrow engraftment and tolerance to multiple gene products," Blood, vol. 108, No. 6, (2006), pp. 1841-1848.
Grossman et al., "Differential expression of granzymes A and B in human cytotoxic lymphocyte subsets and T regulatory cells," Blood, vol. 104, (2004), pp. 2840-2848.

(56) References Cited

OTHER PUBLICATIONS

Haque, "Cysteinylation of MHC Class II Ligands: Peptide Endocytosis and Reduction Within APC Influences T Cell Recognition. sup.1," (2001) J. Immunol. 166, 4543-4551.
Harris et al., "Prediction of murine MHC class I epitopes in a major house dust mite allergen and induction of T1-type CD8+ T cell responses," (1997) Int. Immunol., vol. 9, No. 2, 273-280.
Haveman et al., "Induction and capture of CD4+ cytotoxic adenoviral specific T-cells in response to pan-DR binding adenoviral epitopes toward immunotherapy," Blood, vol. 106, (2005), Abstract 3238.
Haveman et al., "Novel pan-DR-binding T cell epitopes of adenovirus induce pro-inflammatory cytokines and chemokines in healthy donors," Int Immunol. 18(11):1521-1529 (2006).
Heemskerk et al., "Adenovirus-Specific CD4.sup.+ T Cell Clones Recognizing Endogenous Antigen Inhibit Viral Replication In Vitro through Cognate Interaction," The Journal of Immunology (2006); 177:8851-8859.
Ho et al., "CD4(−)CD8alphaalpha subset of CD1d-restricted NKT cells controls T cell expansion," J Immunol. 172(12):7350-8 (2004).
Hohn et al., "CD4+ tumor-infiltrating lymphocytes in cervical cancer recognize HLA-DR-restricted peptides provided by human papillomavirus-E7," J. Immunol., vol. 163, (1999), pp. 5715-5722.
Hori et al., "Control of regulatory T cell development by the transcription factor Foxp3," Science, vol. 299, (2003), pp. 1057-1061.
Hsu et al., "Assessing computational amino acid—turn propensities with a phage-displayed combinatorial library and directed evolution," Structure, (2006), vol. 14, pp. 1499-1510.
Iqbalsyah et al., "The CXXC motif at the N terminus of an .alpha.-helical peptide," (2006) Protein Sci. 15, 1945-1950.
Ise et al., "Naive CD4+ T cells exhibit distinct expression patterns in cytokines and cell surface molecules on their primary responses to varying doses of antigen," J. Immunol., vol. 168, (2002), pp. 3242-3250.
James et al., "HY peptides modulate transplantation responses to skin allografts," Int Immunol. 14(11):1333-1342 (2002).
Janeway et al., Immunobiology, 3rd edition, Garland Press Inc., 1997, p. G: 11.
Janssens et al., "CD4+ CD25+ T Cells Lyse Antigen-Presenting B Cells by Fas-Fas Ligand Interaction in an Epitope-Specific Manner. sup.1," (2003) J. Immunol. 171, 4604-4612.
Jensen, "Acidification and Disulfide Reduction Can be Sufficient to Allow Intact Proteins to Bind MHC," (1993) J. Immunol. 150, No. 8, 3347-3356.
Joffre et al., "Induction of antigen-specific tolerance to bone marrow allografts with CD4+CD25+ T lymphocytes," Blood, vol. 103, No. 11, (2004), pp. 4216-4221.
Karin et al., "Reversal of Experimental Autoimmune Encephalomyelitis by a Soluble Peptide Variant of a Myelin Basic Protein Epitope: T Cell Receptor Antagonism and Reduction of Interferon γ and Tumor Necrosis Factor α Production," J Exp Med. Dec. 1, 1994;180(6):2227-37.
Kasprowicz et al., "Tracking of Peptide-Specific CD4+ T-Cell Responses After and Acute Resolving Viral Infection: a Study of Parovirus 819," Journal of Virology, Nov. 2006, vol. 80, No. 22, pp. 11209-11217.
Khare et al., "HLA class II transgenic mice authenticate restriction of myelin oligodendrocyte glycoprotein-specific immune response implicated in multiple sclerosis pathogenesis," (2003) Int. Immunol. 15, No. 4, 535-546.
Klebanoff et al.,"Therapeutic cancer vaccines: are we there yet?" Immunol. Rev. (2011), 239: 27-44.
Kumar et al., "Twins and endocrinology," Indian J Endocrinol Metab. Nov. 2014;18(Suppl 1):S48-52. doi: 10.4103/2230-8210. 145074.
Lewin et al., "Effects of substitutions in the CXXC active-site motif of the extracytoplasmic hioredoxin ResA," Biochem. J. (2008), 414, 81-91.
Li et al., "Twisting immune responses for allogeneic stem cell therapy," (2009) World J Stem Cells 1(1), 30-35.

Li Pira et al., "High throughput T epitope mapping and vaccine development," The Journal of Biomedicine and Technology, (2010), vol. 2010, 12 pages.
Lindqvist et al., "Both CD4+ FoxP3+ and CD4+ FoxP3− T cells from patients with B-cell malignancy express cytolytic markers and kill autologous leukaemic B cells in vitro," Immunology 133:296-306 (2011).
Louis et al., "Contrasting CD25hiCD4+ T cells/FOXP3 patterns in chronic rejection and operational drug-free tolerance," Transplantation, vol. 81, (2006), pp. 398-407.
Mach et al., "Regulation of MHC Class II Genes: Lessons from a Disease," (1996) Ann. Rev. Immunol. 14, 301-331.
Maeda et al., "CD1d-independent NKT cells in beta 2-microglobulin-deficient mice have hybrid phenotype and function of NK and T cells," J. Immunol., vol. 172, (2004), pp. 6115-6122.
Maekawa et al., "Evidence for a Domain-Swapped CD4 Dimer as the Coreceptor for Binding to Class II MHC," (2006) J. Immunol. 176(11), 6873-6878.
Markovic-Plese et al., "T cell recognition of immunodominant and cryptic proteolipid protein epitopes in humans," J Immunol. 155(2):982-92 (1995) (12 pages).
Marti et al., "Conformationally Correct Expression of Membrane-Anchored Toxoplasma gondii SAG1 in the Primitive Protozoan Giardia duodenalis," Infection and Immunity, vol. 70, No. 2, Feb. 2002, p. 1014-1016.
Massilamany et al., "Detection of autoreactive CD4 T cells using major histocompatibility complex class II dextramers," BMC Immunology, (2011), 12:40.
Matsuda et al., "CD1 d-reslricted iNKT cells, the 'Swiss-Army Knife' of the immune system," Current Opinion in Immunology, vol. 20, No. 3, Jun. 1, 2008, pp. 358-368.
Matthias et al, "Disulfide exchange in domain 2 of CD4 is required for entry of HIV-1," (2002) Nature Immunol 3, No. 8, 727-732.
Maynard et al., "Regulatory T cells expressing interleukin 10 develop from Foxp3+ and Foxp3− precursor cells in the absence of interleukin 10," Nat. Immunol., vol. 8, (2007), pp. 931-941.
MedlinePlus Medical Dictionary (Merriam Webster, Inc., 2017).
Merkler et al., "Myelin oligodendrocyte glycoprotein-induced experimental autoimmune encephalomyelitis in the common marmoset reflects the immunopathology of pattern II multiple sclerosis lesions," Multiple Sclerosis 12:369-374 (2006).
Moldovan et al., "CD4 Dimers Constitute the Functional Component Required for T Cell Activation," The Journal of Immunology (2002), 169:6261-6268.
Nepom, "MHC class II tetramers," The Journal of Immunology, (2012), 188, 2477-2482.
Nielsen et al., "Quantitative Predictions of Peptide Binding to Any HLA-DR Molecule of Known Sequence: NetMHCIIpan," PLOS Comp. Biol., 2008 4(7): 4(7): e1000107.
Ochoa-Garay et al., "The Ability of Peptides to Induce Cytotoxic T Cells In Vivo Does Not Strongly Correlate With Their Affinity for the H-2L$^d$ Molecule: Implications For Vaccine Design and Immunotherapy," Mol Immunol (1997) 34(3):273-81.
Okubo et al., "Analysis of HLA-DRB1 0901-binding HPV-16 E7 helper T cell epitopel," (2004) J Obstet Gynaecol Res. 30(2), 120-129.
Oliviera et al., "Insights into the Specificity of Thioredoxin Reductase—Thioredoxin Interactions. A Structural and Functional Investigation of the Yeast Thioredoxin System," (2010) Biochemistry 49, 3317-3326.
Papanastasiou et al. "Primary structure and biochemical properties of a variant-specific surface protein of Giardia," Molecular and Biochemical Parasitology 86 (1997) 13-27.
Park et al., "Redox Regulation Facilitates Optimal Peptide Selection by MHC Class I during Antigen Processing," Cell, (2006), 127:369-382.
Peterson, "Regulatory T-cells, diverse phenotypes integral to immune homeostasis and suppression," Toxic Path. 40(2):186-204 (2012).
Printout from NetM HCIIpan Server—prediction results dated Sep. 26, 2018, one page.
Qin et al., "Fusion protein of CDR mimetic peptide with Fc inhibit TNF-alpha induced cytotoxicity," Mol. Immunol., vol. 43, (2006), pp. 660-666.

(56) References Cited

OTHER PUBLICATIONS

Quintana et al., "Epitope spreading as an early pathogenic event in pediatric multiple sclerosis," Neurology 83(24):2219-26 (2014).
Rammensee et al., "MHC Ligands and Peptide Motifs," 1997, Springer, New York & Austin, Texas, USA, p. 317.
Rancaniello, "How many viruses on earth?" Virology Blog (2013), http://www.virology.ws/2013/09/06/how-many-viruses-on-earth/.
Reznik et al., "Indirect Allorecognition of Mismatched Donor HLA Class II Peptides in Lung Transplant Recipients with Bronchiolitis Obliterans Syndrome," 2001, Am. J. Transpl. vol. 1: 228-235.
Robinson, Vaccine Protocol (Humana Press, 2003, Totowa, NJ, Ed. Andrew Robinson, Michael J. Hudson and Martin P. Cranage, pp. 121-123).
Roep et al., "The problems and promises of research into human immunology and autoimmune disease," (2012) Nature Med 18(1) 48-53.
Roopenian et al., "The immunogenomics of minor histocompatibility antigens," Immunol. Rev., vol. 190, (2002), pp. 86-94.
Roper et al., "SARS vaccines: where are we?", 2009, Expert Review of Vaccines, vol. 8, pp. 887-898.
Saez-Borderias et al, "Expression and function of NKG2D in CD4+ T cells specific for human cytomegalovirus," Eur. J. Immunol., vol. 36, (2006), pp. 3198-3206.
Santin et al., "Human Papillomavirus Type 16 and 18 E7-Pulsed Dendritic Cell Vaccination of Stage IB or IIA Cervical Cancer Patients: a Phase I Escalating-Dose Trial," (2008) J. Virol. 82, No. 4, 1968-1979.
Savoldo et al., "Generation of EBV-Specific CD4+ Cytotoxic T Cells from Virus Naive Individuals.sup.1," (2002) J Immunol. 168(2), 909-918.
Schrieber et al., "Tumor immunogenicity and responsiveness to cancer vaccine therapy: The state of the art," Seminar. Immunol. 22:105-112, (2010).
Schultz et al., "A MAGE-A3 Peptide Presented by HLA-DP4 Is Recognized on Tumor Cells by CD4+ Cytolytic T Lymphocytes1," Cancer Research 60, 6272-6275, Nov. 16, 2000.
Sette et al., "HLA supertypes and supermotifs: a functional perspective on HLA polymorphism," (1998) Curr Opinion Immunol. 10, 478-482.
Sette et al., "Epitope-based vaccines: an update on epitope identification, vaccine design and delivery," 2003, Current Opinion in Immunology, vol. 15, pp. 461-470.
Shi et al., "A novel plasma membrane-bound thioredoxin from soybean," (1996) Plant Mol. Biol. 32, 653-662 (Abstract).
Stenstrom et al., "Natural killer T-cell populations in C57BL/6 and NK1.1 congenic BALB.NK mice—a novel thymic subset defined by BALB.NK mice," Immunology, vol. 114, (2005), pp. 336-345.
Straub et al., "Allelic variation in GAD1 (GAD67) is associated with schizophrenia and influences cortical function and gene expression," Molecular Psychiatry (2007) 12, 854-869.
Sundar et al., "Generation of Epstein-Bar virus antigen-specific suppressor T cells in vitro," Int. J. Cancer, vol. 35, (1985), pp. 351-357.
Taylor et al., "T regulatory cells and allergy," Microbes and Infection, vol. 7, (2005), pp. 1049-1055.
Texier et al., "On the diversity and heterogeneity of H-2.sup.d-restricted determinants and T cell epitopes from the major bee venom allergen," (1999) Int Immunol. 11, 1313-1325.
Thomson et al., "Targeting a Polyepitope Protein Incorporating Multiple Class II-Restricted Viral Epitopes to the Secretory/Endocytic Pathway Facilitates Immune Recognition by CD4+ Cytotoxic T Lymphocytes: a Novel Approach to Vaccine Design," J. of Virol, 1998, 72(3):2246-2252.
Tindle et al., "A "public" T-helper epitope of the E7 transforming protein of human papillomavirus 16 provides cognate help for several E7 B-cell epitopes from cervical cancer-associated human papillomavirus genotypes," (1991) Proc Natl. Acad. Sci 88, 5887-5891.
Tisch et al., "Antigen-specific immunotherapy: Is it a real possibility to combat T-cell-mediated autoimmunity?" PNAS 91: 437-438, (1994).
Toyokawa et al., "Relative Contribution of Direct and Indirect Allorecognition in Developing Tolerance After Liver Transplantation," 2008 Liver Transpl. 14(3) 346-357.
Tsuji et al., "Antigen-specific, CD4+CD25+ regulatory T cell clones induced in Peyer's patches," Int. Immunol., vol. 15, (2003),pp. 525-534.
UniProt P01906.2, 2017, p. 1-6.
UniProt 015523.2, 2017, pp. 1-7.
Voo et al., "Functional characterization of EBV-encoded nuclear antigen 1-specific CD4+ helper and regulatory T cells elicited by in vitro peptide stimulation," Cancer Res., vol. 65, (2005), pp. 1577-1586.
Wang et al., "Generation and characterization of HLA-A*2.1 restricted and Prostein 31-39 specific NKT cell lines," Acta Academiae Medicine Militaris Tertiae. 28(16):1652-1655 (2006) (English language translation provided) (11 pages).
Wang, "Immune suppression by tumor-specific CD4+ regulatory T-cells in cancer," Semin. Cancer Biol., vol. 16, (2006), pp. 73-79.
Weissert et al., "MHC Class II-Regulated Central Nervous System Autoaggression and T Cell Responses in Peripheral Lymphoid Tissues Are Dissociated in Myelin Oligodendrocyte Glycoprotein-Induced Experimental Autoimmune Encephalomyelitis.sup.1," (2001) J. Immunol. 166, 7588-7599.
Wekerle et al., "Autoimmunity's next top models," (2012) Nature Med. 18(1), 66-70.
Wiker et al., "Cloning, expression and significance of MPT53 for identification of secreted proteins of *Mycobacterium tuberculosis*," Microb. Pathog., vol. 26, (1999), pp. 207-219.
Wobus et al., "Embryonic Stem Cells: Prospects for Developmental Biology and Cell Therapy," (2005) Physiol Rev 85: 635-678.
Wood et al., "Regulatory T cells in Transplantation tolerance," Nat. Rev. Immunol., vol. 3, (2003), pp. 199-210.
Wooldridge et al., "Tricks with tetramers: how to get the most from multimeric peptide-MHC," Immunology, 2009, 126(2):147-64.
Written Description Training Materials, Revision 1, Mar. 25, 2008, U.S. Patent and Trademark Office.
Wu et al., "Engineering an intracellular pathway for major histocompatibility complex class II presentation of antigens," (1995) Proc. Natl. Acad. Sci. 92, 11671-11675.
Zeng at al., "Crystal structure of mouse CD1: An MHC-like fold with a large hydrophobic binding groove," Science 277: 339-345 (1997).
Zhang et al., "A MAGE-3 Peptide Presented by HLA-DR1 to CD4+ T Cells That Were Isolated from a Melanoma Patient Vaccinated with a MAGE-3 Protein," J Immunol. 171:219-225 (2003).
Zhao et al., "Activated CD4+CD25+ T cells selectively kill B Lymphocytes," Blood, vol. 107, No. 10; pp. 3925-3932; May 15, 2006.

* cited by examiner

IMMUNOGENIC CD1D BINDING PEPTIDES

CROSS-REFERENCE TO RELATED APPLICATIONS

This application is a U.S. national stage entry under 35 U.S.C. § 371 of PCT International Patent Application No. PCT/EP2017/059302, filed Apr. 19, 2017, which claims priority to European Patent Application No. 16166054.3, filed Apr. 19, 2016, the contents of each of which are incorporated herein by reference in their entirety.

REFERENCE TO SEQUENCE LISTING SUBMITTED ELECTRONICALLY

The content of the electronically submitted sequence listing (Name: 2752.0122_Sequence_Listing_ST25.txt; Size: 32.8 kilobytes; and Date of Creation: Jul. 9, 2021) filed on Mar. 30, 2021 is incorporated herein by reference in its entirety.

FIELD OF THE INVENTION

The present invention relates to immunogenic peptides. The peptides are used in in vitro and in vivo systems to generate antigen specific cytolytic NKT cells. The peptides and cells obtained by these peptides are used as pharmaceutically active peptides for a variety of disorders including auto immune diseases such as multiple sclerosis.

BACKGROUND OF THE INVENTION

WO2012069568 discloses a novel class of peptides which comprise a CD1d binding peptide of an antigen and a redox motif sequence.

Redox motif sequences have been reviewed in Fomenko et al. (2003) *Biochemistry* 42, 11214-11225. The different alternatives of the redox motif sequence are C-(X)2-C [SEQ ID NO:13], C-(X)2-S [SEQ ID NO: 14, C-(X)2-T [SEQ ID NO: 15], S-(X)2-C [SEQ ID NO:16], and T-(X)2-C [SEQ ID NO:17]. Other prior art on redox motif sequences comments on the relevance of a histidine within the redox motif sequence [Kortemme et al. (1996) *Biochemistry* 35, 14503-14511].

WO2012069568 explains that the combination of a CD1d binding peptide epitope and a redox motif sequence in each other's proximity within a peptide provides properties which have not been recognised before. Namely, such peptides have the capacity to elicit a population of antigen specific NKT cells which kill specifically the antigen presenting cells which present the antigen comprising the CD1d binding peptide epitope which is present in the peptide.

Consequently these peptides can be used to block an immune response at a very early stage, i.e. at the level of antigen presentation. WO 2012/069568 demonstrates the medical use of these peptides. The concept of the invention has been later published in Carlier et al. (2012) *Plos one* 7,10 e45366.

This publication discusses the type of redox motif sequence and the spacing between redox motif and CD1d epitope sequence. Further determinants in the peptides which may provide improved properties to the peptides have not been reported.

SUMMARY OF THE INVENTION

The different alternatives of the 4 amino acid redox motif sequence as mentioned in the introduction can also written as [CST]-X(2)-C [SEQ ID NO:54] or C-X(2)-[CST] [SEQ ID NO:55]. The present invention reveals that the presence of an additional histidine or tryptophan amino acid immediately adjacent outside the motif (N terminal of the motif (position −1) or C-terminal of the motif (position +5)) increases the stability of the redox motif. Thus, the present invention relates to modified redox motifs with general structure [HW]-C-X(2)-[CST] [SEQ ID NO:1] or [CST]-X(2)-C-[HW] [SEQ ID NO:4].

With this improved stability the specific reducing activity of the peptide increases, such that for example less peptide can be used or the number of injections is reduced, compared to a peptide wherein the additional histidine or tryptophan is not present. A first aspect relates to isolated immunogenic peptide a of between 12 and 100 amino acids comprising a CD1d binding peptide epitope of an antigen, and immediately adjacent or separated by at most 7 amino acids from said epitope a [HW]-X(0,2)-C-X(2)-[CST] ([SEQ ID NO: 1], [SEQ ID NO:2], [SEQ ID NO:3]) or a [CST]-X(2)-C-X(0,2)-[HW] [SEQ ID NO:4], [SEQ ID NO:5], [SEQ ID NO:6] redox motif sequence for use as a medicament.

In certain embodiment said antigen does not contain in its sequence said motif within a distance of 10 amino acids of said epitope, or even does not contain in its sequence said motif.

In specific embodiments the motif is H-X-C-X(2)-[CST] [SEQ ID NO:56], [CST]-X(2)-C-X-H [SEQ ID NO: 57], [CST]-X(2)-C-X-W [SEQ ID NO: 58], or W-X-C-X(2)-[CST] [SEQ ID NO:59].

In other embodiments the motif is [HW]-X(0,2)-C-X(2)-C ([SEQ ID NO:7], [SEQ ID NO:8], [SEQ ID NO:9]), or C-X(2)-C-X(0,2)-[HW] ([SEQ ID NO:10], [SEQ ID NO:11], [SEQ ID NO:12]).

In yet other embodiments the motif is [HW]-C-X(2)-C [SEQ ID NO:7] or C-X(2)-C-[HW] [SEQ ID NO:10], namely H-C-X(2)-C [SEQ ID NO: 48], C-X(2)-C-H [SEQ ID NO:42], W-C-X(2)-C [SEQ ID NO: 51] or C-X(2)-C-W [SEQ ID NO:45].

In specific embodiments, the peptides have a length of between 12 and 75 amino acids, between 12 and 50 amino acids, or between 12 and 30 amino acids.

The CD1d binding peptide, can be separated from said motif by a sequence of at most 4 amino acids, e.g. by a sequence of 2 amino acids.

In specific embodiments, wherein X within the redox motif is Gly or Pro, or X within the redox motif is not Cys.

In other specific embodiment, X outside the redox motif is not Cys, Ser or Thr. Another aspect relates to isolated immunogenic peptides of between 12 and 100 amino acids comprising a CD1d binding peptide of an antigen, and immediately adjacent or separated by at most 7 amino acids from said epitope a [HW]-X(0,2)-C-X(2)-[CST] ([SEQ ID NO: 1], [SEQ ID NO: 2], [SEQ ID NO:3]) or [CST]-X(2)-C-X(0,2)-[HW] [SEQ ID NO:4], [SEQ ID NO:5], [SEQ ID NO:6]) redox motif sequence, with the proviso that said antigen does not contain in its sequence said motif within a distance of 10 amino acids of said epitope.

In certain embodiment the antigen does not contain in its sequence said motif. Specific embodiments of motifs are [HW]-X-C-X(2)-[CST] [SEQ ID NO:2], [CST]-X(2)-C-X-[HW] [SEQ ID NO:5], [HW]-C-X(2)-[CST] [SEQ ID NO:1] or [CST]-X(2)-C-[HW] [SEQ ID NO:4],

[HW]-X(0,2)-C-X(2)-C ([SEQ ID NO:7], [SEQ ID NO:8], [SEQ ID NO:9]), C-X(2)-C-X(0,2)-[HW] ([SEQ ID NO:10], [SEQ ID NO:11], [SEQ ID NO:12]) [HW]-C-X(2)-C [SEQ ID NO:7] or C-X(2)-C-[HW] [SEQ ID NO:10].

In specific embodiments of peptides, if said motif is [HW]-X(0,2)-C-X(2)-[CST], ([SEQ ID NO:1], [SEQ ID NO:2], [SEQ ID NO:3]) the motif is located N terminally from the CD1d binding peptide epitope within the peptide, and wherein, if said motif is [CST]-X(2)-C-X(0,2)-[HW] ([SEQ ID NO:4], [SEQ ID NO:5], [SEQ ID NO:6]), the motif is located C terminally from the CD1d binding peptide epitope.

The motif can be located N terminally from the CD1d binding peptide epitope. The peptides can have a length of between 12 and 75 amino acids, of between 12 and 50 amino acids, of between 12 and 30 amino acids.

In specific embodiments, the CD1d binding peptide, is separated from said motif by a sequence of at most 4 amino acids or is separated from said motif by sequence of 2 amino acids.

In specific embodiments X within the redox motif is Gly or Pro, or X within the redox motif is not Cys.

In specific embodiments X outside the redox motif is not Cys, Ser or Thr.

Another aspect are methods of treatment or prevention comprising the step of administering an effective amount of an immunogenic peptide of between 12 and 100 amino acids comprising a CD1d binding peptide of an antigen, and immediately adjacent or separated by at most 7 amino acids from said epitope a [HW]-X(0,2)-C-X(2)-[CST] ([SEQ ID NO:1], [SEQ ID NO:2], [SEQ ID NO:3]) or a [CST]-X(2)-C-X(0,2)-[HW] ([SEQ ID NO:4], [SEQ ID NO:5], [SEQ ID NO:6]) redox motif sequence. Another aspect of the invention relates to in vitro use of a described above for the generation of antigen specific NKT cells.

Another aspect relates to a method for obtaining a population NKT cells which are cytolytic against cells presenting an antigen, the method comprising the steps of: providing peripheral blood cells; contacting said cells in vitro with an immunogenic peptide of between 12 and 100 amino acids comprising a CD1d binding peptide of an antigen, and immediately adjacent or separated by at most 7 amino acids from said epitope a [HW]-X(0,2)-C-X(2)-[CST] ([SEQ ID NO:1], [SEQ ID NO:2], [SEQ ID NO:3]) or a [CST]-X(2)-C-X(0,2)-[HW] ([SEQ ID NO:4], [SEQ ID NO:5], [SEQ ID NO:6]) redox motif sequence; and expanding said cells in the presence of IL-2. Another aspect relates to a population of cells obtainable by the above method of for use as a medicament.

Another aspect relates to methods of treatment and prevention comprising the step of administering an effective amount of cells as described above.

The invention relates to an isolated immunogenic peptide of between 12 and 100 amino acids comprising a CD1d binding peptide epitope of an antigen with a [FWYHT]-X(2)-[VILM]-X(2)-[FWYHT] [SEQ ID NO:60] sequence motif, and immediately adjacent or separated by at most 7 amino acids from said epitope a [HW]-X(0,2)-C-X(2)-[CST] ([SEQ ID NO:1], [SEQ ID NO:2], [SEQ ID NO:3]), or a [CST]-X(2)-C-X(0,2)-[HW] ([SEQ ID NO:4], [SEQ ID NO:5], [SEQ ID NO:6]) redox motif sequence for use as a medicament, with the proviso that said peptide does not contain in its sequence an MHC class II T-cell epitope.

In embodiments thereof, said antigen does not contain in its sequence said CD1d binding peptide motif within a distance of 10 amino acids of said epitope.

In embodiments thereof wherein the CD1d binding peptide sequence motif is [FWY]-X(2)-[VILM]-X(2)-[FWY] [SEQ ID NO:63].

In embodiments thereof the redox motif is [HW]-X-C-X(2)-[CST] [SEQ ID NO:2] or [CST]-X(2)-C-X-[HW] [SEQ ID NO: 5].

In embodiments thereof the redox motif is [HW]-C-X(2)-[CST] [SEQ ID NO:1] or [CST]-X(2)-C-[HW] [SEQ ID NO:4].

In embodiments thereof the redox motif is H-C-X(2)-[CST] [SEQ ID NO:101] or [CST]-X(2)-C-H [SEQ ID NO:102].

In embodiments thereof the redox motif is [HW]-X(0,2)-C-X(2)-C ([SEQ ID NO:7], [SEQ ID NO:8], [SEQ ID NO:9]) or C-X(2)-C-X(0,2)-[HW] ([SEQ ID NO:10], [SEQ ID NO:11], [SEQ ID NO:12]).

In embodiments thereof the redox motif is [HW]-C-X(2)-C [SEQ ID NO:7] or C-X(2)-C-[HW] [SEQ ID NO:10].

In embodiments thereof the redox motif is H-C-X(2)-C [SEQ ID NO:48] or C-X(2)-C-H [SEQ ID NO: 42].

In embodiments thereof said peptide has a length of between 12 and 50 amino acids. In embodiments thereof X within the redox motif is Gly or Pro, or X within the redox motif is not Cys, or X outside the redox motif is not Cys, Ser or Thr.

The invention further relates to an isolated immunogenic peptide of between 12 and 100 amino acids comprising a CD1d binding peptide of an antigen with a [FWYHT]-X(2)-[VILM]-X(2)-[FWYHT] [SEQ ID NO:60] sequence motif, and immediately adjacent or separated by at most 7 amino acids from said epitope a [HW]-X(0,2)-C-X(2)-[CST] ([SEQ ID NO:1], [SEQ ID NO:2], [SEQ ID NO:3]) or [CST]-X(2)-C-X(0,2)-[HW] ([SEQ ID NO:4], [SEQ ID NO:5], [SEQ ID NO:6]) redox motif sequence, with the proviso that said peptide does not contain in its sequence an MHC class II T-cell epitope.

In embodiments thereof said antigen does not contain in its sequence said CD1d binding peptide motif within a distance of 10 amino acids of said redox motif sequence.

In embodiments thereof said antigen does not contain in its sequence said CD1d binding peptide motif.

In embodiments thereof the redox motif is [HW]-X-C-X(2)-[CST] [SEQ ID NO:2] or a [CST]-X(2)-C-X-[HW] [SEQ ID NO:5].

In embodiments thereof, the redox motif sequence is [HW]-C-X(2)-[CST] [SEQ ID NO:1] or [CST]-X(2)-C-[HW] [SEQ ID NO:4].

In embodiments thereof the redox motif sequence is H-C-X(2)-[CST] [SEQ ID NO: 101] or [CST]-X(2)-C-H [SEQ ID NO: 102].

In embodiments thereof

- if said redox motif is [HW]-X(0,2)-C-X(2)-[CST], ([SEQ ID NO:1], [SEQ ID NO:2], [SEQ ID NO:3]) the redox motif is located N terminally from the CD1d binding peptide epitope within the peptide, and wherein,
- if said redox motif is [CST]-X(2)-C-X(0,2)-[HW] ([SEQ ID NO:4], [SEQ ID NO:5], [SEQ ID NO:6]) the redox motif is located C terminally from the CD1d binding peptide epitope within the peptide.

In embodiments thereof the redox motif is [HW]-X(0,2)-C-X(2)-C ([SEQ ID NO:7], [SEQ ID NO:8], [SEQ ID NO:9]) or C-X(2)-C-X(0,2)-[HW] ([SEQ ID NO:10], [SEQ ID NO:11], [SEQ ID NO:12]).

In embodiments thereof the redox motif is [HW]-C-X(2)-C [SEQ ID NO:7] or C-X(2)-C-[HW] [SEQ ID NO:10].

In embodiments thereof the redox motif is H-C-X(2)-C [SEQ ID NO:48] or C-X(2)-C-H [SEQ ID NO: 42].

In embodiments thereof said redox motif is located N terminally from the CD1d binding peptide epitope.

In embodiments thereof said peptide has a length of between 12 and 50 amino acids. In embodiments thereof X within the redox motif is Gly or Pro, or wherein X within the redox motif is not Cys, or wherein X outside the redox motif is not Cys, Ser or Thr.

The invention further relates to the in vitro use of peptide as described above for the generation of antigen specific cytolytic NKT cells.

The invention further relates for obtaining a population of NKT cells which are cytolytic against cells presenting an antigen with a CD1d binding peptide epitope, the method comprising the steps of:
providing peripheral blood cells;
contacting said cells in vitro with an immunogenic peptide of between 12 and 100 amino acids comprising a CD1d binding peptide epitope of an antigen with a [FWYHT]-X(2)-[VILM]-X(2)-[FWYHT] [SEQ ID NO:60] sequence motif, and immediately adjacent or separated by at most 7 amino acids from said epitope a [HW]-X(0,2)-C-X(2)-[CST] ([SEQ ID NO:1], [SEQ ID NO:2], [SEQ ID NO:3]) or a [CST]-X(2)-C-X(0,2)-[HW] ([SEQ ID NO:4], [SEQ ID NO:5], [SEQ ID NO:6]) redox motif sequence, wherein said peptide does not contain in its sequence an MHC class II T-cell epitope; and
expanding said cells in the presence of IL-2.

The invention further relates to a population of cells obtainable by the above method for use as a medicament.

The invention further relates to a method for preparing a peptide comprising the step of:
identifying within an antigen a sequence with an [FWYHT]-X(2)-[VILM]-X(2)-[FWYHT] [SEQ ID NO:60] sequence motif;
preparing a peptide of between 12 and 100 amino comprising the above identified sequence and immediately adjacent or separated by at most 7 amino acids therefrom a [HW]-X(0,2)-C-X(2)-[CST] ([SEQ ID NO:1], [SEQ ID NO:2], [SEQ ID NO:3]) or [CST]-X(2)-C-X(0,2)-[HW] ([SEQ ID NO:4], [SEQ ID NO:5], [SEQ ID NO:6]) redox motif sequence,
with the proviso that the prepared sequence does not contain in its sequence an MHC class II T-cell epitope.

DETAILED DESCRIPTION

Definitions

The term "peptide" as used herein refers to a molecule comprising an amino acid sequence of between 2 and 200 amino acids, connected by peptide bonds, but which can comprise non-amino acid structures. Peptides according to the invention can contain any of the conventional 20 amino acids or modified versions thereof, or can contain non-naturally occurring amino-acids incorporated by chemical peptide synthesis or by chemical or enzymatic modification. The term "antigen" as used herein refers to a structure of a macromolecule, typically protein (with or without polysaccharides) or made of proteic composition comprising one or more hapten(s) and comprising T cell epitopes. The term "antigenic protein" as used herein refers to a protein comprising one or more T cell epitopes. An "auto-antigen" or "auto-antigenic protein" as used herein refers to a human or animal protein present in the body, which elicits an immune response within the same human or animal body. The term "food or pharmaceutical antigenic protein" refers to an antigenic protein present in a food or pharmaceutical product, such as in a vaccine. The term "T cell epitope" in the context of the present invention refers to a dominant, sub-dominant or minor T cell epitope, i.e. a part of an antigenic protein that is specifically recognised and bound by a receptor at the cell surface of a T lymphocyte. Whether an epitope is dominant, sub-dominant or minor depends on the immune reaction elicited against the epitope. Dominance depends on the frequency at which such epitopes are recognised by T cells and able to activate them, among all the possible T cell epitopes of a protein.

The T cell epitope is an epitope recognised by MHC class II molecules, which consists of a sequence of 8 or, typically 9 amino acids which fit in the groove of the MHC II molecule. Within a peptide sequence representing a T cell epitope, the amino acids in the epitope are numbered P1 to P9, amino acids N-terminal of the epitope are numbered P−1, P−2 and so on, amino acids C terminal of the epitope are numbered P+1, P+2 and so on. Peptides recognised by MHC class II molecules and not by MHC class I molecules are referred to as MHC class II restricted T cell epitopes. Methods to identify MHC class II T cell epitopes are described below.

The term "CD1d-restricted NKT cell peptide epitope" refers to a part of an antigenic protein that is specifically bound by a CD1d molecule, expressed at cell surface and recognized by a NKT cell.

The CD1d-restricted NKT cell peptide epitope has a general motif [FWYHT]-X(2)-[VILM]-X(2)-[FWYHT] [SEQ ID NO:60]. Alternative versions of this general motif have at position 1 and/or position 7 the alternatives [FWYH], thus [FWYH]-X(2)-[VILM]-X(2)-[FWYH] [SEQ ID NO:61].

Alternative versions of this general motif have at position 1 and/or position 7 the alternatives [FWYT], [FWYT]-X(2)-[VILM]-X(2)-[FWYT] [SEQ ID NO:62]. Alternative versions of this general motif have at position 1 and/or position 7 the alternatives [FWY], [FWY]-X(2)-[VILM]-X(2)-[FWY] [SEQ ID NO:63].

Regardless of the amino acids at position 1 and/or 7, alternative versions of the general motif have at position 4 the alternatives [ILM], e.g. [FWYH]-X(2)-[ILM]-X(2)-[FWYH] [SEQ ID NO:64] or [FWYHT]-X(2)-[ILM]-X(2)-[FWYHT] [SEQ ID NO:65] or [FWY]-X(2)-[ILM]-X(2)-[FWY] [SEQ ID NO:65].

A CD1d binding motif in a protein can be identified by scanning a sequence for the above sequence motifs, either by hand, either by using an algorithm such as ScanProsite De Castro E. et al. (2006) *Nucleic Acids Res.* 34(Web Server issue):W362-W365.

"Natural killer T" or "NKT" cells constitute a distinct subset of non-conventional T lymphocytes that recognize antigens presented by the non-classical MHC complex molecule CD1d. Two subsets of NKT cells are presently described. Type I NKT cells, also called invariant NKT cells (iNKT), are the most abundant. They are characterized by the presence of an alpha-beta T cell receptor (TCR) made of an invariant alpha chain, Valpha14 in the mouse and Valpha24 in humans. This alpha chain is associated to a variable though limited number of beta chains. Type 2 NKT cells have an alpha-beta TCR but with a polymorphic alpha chain. However, it is apparent that other subsets of NKT cells exist, the phenotype of which is still incompletely defined, but which share the characteristics of being activated by gly-colipids presented in the context of the CD1d molecule.

NKT cells typically express a combination of natural killer (NK) cell receptor, including NKG2D and NK1.1. NKT cells are part of the innate immune system, which can be distinguished from the adaptive immune system by the fact that they do not require expansion before acquiring full effector capacity. Most of their mediators are preformed and do not require transcription. NKT cells have been shown to be major participants in the immune response against intracellular pathogens and tumor rejection. Their role in the control of autoimmune diseases and of transplantation rejection is also advocated.

The recognition unit, the CD1d molecule, has a structure closely resembling that of the MHC class I molecule, including the presence of beta-2 microglobulin. It is characterized by a deep cleft bordered by two alpha chains and containing highly hydrophobic residues, which accepts lipid chains. The cleft is open at both extremities, allowing it to accommodate longer chains. The canonical ligand for CD1d is the synthetic alpha galactosylceramide (alpha GalCer). However, many natural alternative ligands have been described, including glyco- and phospholipids, the natural lipid sulfatide found in myelin, microbial phosphoinositol mannoside and alpha-glucuronosylceramide. The present consensus in the art (Matsuda et al (2008), *Curr. Opinion Immunol.*, 20 358-368; Godfrey et al (2010), *Nature rev. Immunol* 11, 197-206) is still that CD1d binds only ligands containing lipid chains, or in general a common structure made of a lipid tail which is buried into CD1d and a sugar residue head group that protrudes out of CD1d.

The term "homologue" as used herein with reference to the epitopes used in the context of the invention, refers to molecules having at least 50%, at least 70%, at least 80%, at least 90%, at least 95% or at least 98% amino acid sequence identity with the naturally occurring epitope, thereby maintaining the ability of the epitope to bind a CD1d molecule. Particular homologues of an epitope correspond to the natural epitope modified in at most three, more particularly in at most 2, most particularly in one amino acid.

The term "derivative" as used herein with reference to the peptides of the invention refers to molecules which contain at least the peptide active portion (i.e. capable of eliciting cytolytic NKT cell activity) and, in addition thereto comprises a complementary portion which can have different purposes such as stabilising the peptides or altering the pharmacokinetic or pharmacodynamic properties of the peptide.

The term "sequence identity" of two sequences as used herein relates to the number of positions with identical nucleotides or amino acids divided by the number of nucleotides or amino acids in the shorter of the sequences, when the two sequences are aligned. In particular, the sequence identity is from 70% to 80%, from 81% to 85%, from 86% to 90%, from 91% to 95%, from 96% to 100%, or 100%. The terms "peptide-encoding polynucleotide (or nucleic acid)" and "polynucleotide (or nucleic acid) encoding peptide" as used herein refer to a nucleotide sequence, which, when expressed in an appropriate environment, results in the generation of the relevant peptide sequence or a derivative or homologue thereof. Such polynucleotides or nucleic acids include the normal sequences encoding the peptide, as well as derivatives and fragments of these nucleic acids capable of expressing a peptide with the required activity. The nucleic acid encoding a peptide according to the invention or fragment thereof is a sequence encoding the peptide or fragment thereof originating from a mammal or corresponding to a mammalian, most particularly a human peptide fragment.

The term "immune disorders" or "immune diseases" refers to diseases wherein a reaction of the immune system is responsible for or sustains a malfunction or non-physiological situation in an organism. Included in immune disorders are, inter alia, allergic disorders and autoimmune diseases.

The terms "allergic diseases" or "allergic disorders" as used herein refer to diseases characterised by hypersensitivity reactions of the immune system to specific substances called allergens (such as pollen, stings, drugs, or food). Allergy is the ensemble of signs and symptoms observed whenever an atopic individual patient encounters an allergen to which he has been sensitised, which may result in the development of various diseases, in particular respiratory diseases and symptoms such as bronchial asthma. Various types of classifications exist and mostly allergic disorders have different names depending upon where in the mammalian body it occurs. "Hypersensitivity" is an undesirable (damaging, discomfort-producing and sometimes fatal) reaction produced in an individual upon exposure to an antigen to which it has become sensitised; "immediate hypersensitivity" depends of the production of IgE antibodies and is therefore equivalent to allergy.

The terms "autoimmune disease" or "autoimmune disorder" refer to diseases that result from an aberrant immune response of an organism against its own cells and tissues due to a failure of the organism to recognise its own constituent parts (down to the sub-molecular level) as "self". The group of diseases can be divided in two categories, organ-specific and systemic diseases. An "allergen" is defined as a substance, usually a macromolecule or a proteic composition which elicits the production of IgE antibodies in predisposed, particularly genetically disposed, individuals (atopics) patients. Similar definitions are presented in Liebers et al. (1996) *Clin. Exp. Allergy* 26, 494-516.

The term "therapeutically effective amount" refers to an amount of the peptide of the invention or derivative thereof, which produces the desired therapeutic or preventive effect in a patient. For example, in reference to a disease or disorder, it is the amount which reduces to some extent one or more symptoms of the disease or disorder, and more particularly returns to normal, either partially or completely, the physiological or biochemical parameters associated with or causative of the disease or disorder. Typically, the therapeutically effective amount is the amount of the peptide of the invention or derivative thereof, which will lead to an improvement or restoration of the normal physiological situation. For instance, when used to therapeutically treat a mammal affected by an immune disorder, it is a daily amount peptide/kg body weight of the said mammal. Alternatively, where the administration is through gene-therapy, the amount of naked DNA or viral vectors is adjusted to ensure the local production of the relevant dosage of the peptide of the invention, derivative or homologue thereof.

The term "natural" when referring to a peptide relates to the fact that the sequence is identical to a fragment of a naturally occurring protein (wild type or mutant). In contrast therewith the term "artificial" refers to a sequence which as such does not occur in nature. An artificial sequence is obtained from a natural sequence by limited modifications such as changing/deleting/inserting one or more amino acids within the naturally occurring sequence or by adding/removing amino acids N- or C-terminally of a naturally occurring sequence.

In this context, it is realised that peptide fragments are generated from antigens, typically in the context of epitope scanning. By coincidence such peptides may comprise in their sequence an MHC class II epitope and in their proximity a sequence with the modified redox motif [HW]-X(0, 2)-C-X(2)-[CST] ([SEQ ID NO:1], [SEQ ID NO:2], [SEQ ID NO:3]) or ([SEQ ID NO:4], [SEQ ID NO:5], [SEQ ID NO:6]). Herein "proximity" means that between MHC class II epitope sequence and between the above [HW]-X(0,2)-C-X(2)-[CST] ([SEQ ID NO:1], [SEQ ID NO:2], [SEQ ID NO:3]) or [CST]-X(2)-C-X(0,2)-[HW] ([SEQ ID NO:4], [SEQ ID NO:5], [SEQ ID NO:6]) motifs, there can be an amino acid sequence of at most 7 amino acids, at most 4 amino acids, at most 2 amino acids, or even 0 amino acids (in other word epitope and motif sequence are immediately adjacent to each other).

Accordingly, specific embodiments of the present invention exclude peptide fragments of antigens which accidentally comprise as well a CD1d binding peptide epitope and a redox motif sequence immediately adjacent to each other or separated by an amino acid sequence of up to 2, 4 or 7 amino acids.

In addition it is realised that certain peptides identified as CD1d binding peptides in view of the presence of the above cited embodiments of a CD1d binding motif, also contain in certain exceptional conditions also a MCH class II T cell epitope. Peptides which include in the sequence a MCH class II T cell epitope are disclaimed from the present invention.

More specifically those peptides are disclaimed wherein such accidental MHC class II peptide resides in the portion of the peptide outside the redox motif sequence. In this case the sequence of the MCH class II T cell epitope and the CD1d binding peptide epitope can partially or completely overlap each other. In the latter case the 7 amino acid sequence of the CD1d binding peptide is completely comprised within the 9 amino acid sequence of an MHC class II T cell epitope.

Peptide fragments of antigens are studied for the immunogenic properties but are generally not used a therapeutic agent (apart from the field of allergy and tumour vaccination). Thus in the absence of any knowledge of the improved properties of the peptides of the present invention the use of such peptides as medicaments is unprecedented.

Amino acids are referred to herein with their full name, their three-letter abbreviation or their one letter abbreviation.

Motifs of amino acid sequences are written herein according to the format of Prosite. Motifs are used to describe a certain sequence variety at specific parts of a sequence. The symbol X is used for a position where any amino acid is accepted. Alternatives are indicated by listing the acceptable amino acids for a given position, between square brackets ('[ ]'). For example: [CST] stands for an amino acid selected from Cys, Ser or Thr. Amino acids which are excluded as alternatives are indicated by listing them between curly brackets ('{ }'). For example: {AM} stands for any amino acid except Ala and Met. The different elements in a motif are separated from each other by a hyphen -. Repetition of an identical element within a motif can be indicated by placing behind that element a numerical value or a numerical range between parentheses. For example: X(2) corresponds to X-X; X(2, 5) corresponds to 2, 3, 4 or 5 X amino acids, A(3) corresponds to A-A-A.

Thus, [HW]-C-X(2)-C [SEQ ID NO:7] can be written as [HW]CXXC.

Similarly C-X(2)-C-X(0,2)-[HW] ([SEQ ID NO:10], [SEQ ID NO:11], [SEQ ID NO:12]) represents the three possibilities wherein there is between C and H or W, none, one or two amino acids; namely C-X(2)-C-[HW] [SEQ ID NO:10], C-X(2)-C-X-[HW] [SEQ ID 11 NO:40] and C-X(2)-C-X(2)-[HW] [SEQ ID NO:12].

Equally [HW]-X(0,2)-C-X(2)-C ([SEQ ID NO:7], [SEQ ID NO:8], [SEQ ID NO:9]) represents the three possibilities wherein there is between H or W and C, none, one or two amino acids, namely [HW]-C-X(2)-C [SEQ ID NO:7], [HW]-X-C-X(2)-C [SEQ ID NO:8] and [HW]-X(2)-C-X(2)-C [SEQ ID NO: 9].

To distinguish between the amino acids X, those between H or W and C are called external amino acids X (single underlined in the above sequence), those within the redox motif are called internal amino acids X (double underlined in the above sequence).

X represents any amino acid, particularly an L-amino acid, more particularly one of the 20 naturally occurring L-amino acids.

A peptide, comprising a CD1d binding peptide epitope and a modified peptide motif sequence, having reducing activity is capable of generating a population of antigen-specific cytolytic NKT cells towards antigen-presenting cells.

Accordingly, in its broadest sense, the invention relates to peptides which comprise at least one CD1d binding peptide epitope of an antigen (self or non-self) with a potential to trigger an immune reaction, and a modified thioreductase sequence motif with a reducing activity on peptide disulfide bonds. The CD1d binding epitope and the modified redox motif sequence may be immediately adjacent to each other in the peptide or optionally separated by one or more amino acids (so called linker sequence). Optionally the peptide additionally comprises an endosome targeting sequence and/or additional "flanking" sequences.

The peptides of the invention comprise a CD1d binding peptide epitope of an antigen (self or non-self) with a potential to trigger an immune reaction, and a modified redox motif. The reducing activity of the motif sequence in the peptide can be assayed for its ability to reduce a sulfhydryl group such as in the insulin solubility assay wherein the solubility of insulin is altered upon reduction, or with a fluorescence-labelled substrate such as insulin. An example of such assay is described in more detail in the experimental section of this application.

The modified redox motif may be positioned at the amino-terminus side of the CD1d binding peptide epitope or at the carboxy-terminus of the CD1d binding peptide epitope.

Peptide fragments with reducing activity are encountered in thioreductases which are small disulfide reducing enzymes including glutaredoxins, nucleoredoxins, thioredoxins and other thiol/disulfide oxydoreductases (Holmgren (2000) *Antioxid. Redox Signal.* 2, 811-820; Jacquot et al. (2002) *Biochem. Pharm.* 64, 1065-1069). They are multifunctional, ubiquitous and found in many prokaryotes and eukaryotes. They exert reducing activity for disulfide bonds on proteins (such as enzymes) through redox active cysteines within conserved active domain consensus sequences: C-X(2)-C [SEQ ID NO:13], C-X(2)-S [SEQ ID NO:14], C-X(2)-T [SEQ ID NO:15], S-X(2)-C [SEQ ID NO:16], T-X(2)-C [SEQ ID NO:17] (Fomenko et al. (2003) *Biochemistry* 42, 11214-11225; Fomenko et al. (2002) *Prot. Science* 11, 2285-2296), in which X stands for any amino acid. Such domains are also found in larger proteins such as protein disulfide isomerase (PDI) and phosphoinositide-specific phospholipase C.

The 4 amino acid redox motif as known from e.g. Fomenko and WO2008/017517 comprises a cysteine at position 1 and/or 4; thus the motif is either C-X(2)-[CST] [SEQ ID NO:55] or [CST]-X(2)-C [SEQ ID NO:54]. Such a tetrapeptide sequence will be referred to as "the motif".

The motif in a peptide can be any of the alternatives C-X(2)-C [SEQ ID NO:13], S-X(2)-C [SEQ ID NO:16], T-X(2)-C [SEQ ID NO:17], C-X(2)-S [SEQ ID NO:14] or C-X(2)-T [SEQ ID NO:15]. In particular, peptides contain the sequence motif C-X(2)-C [SEQ ID NO: 13].

The "modified" redox motif of the peptides of the present invention differs from the prior art in that immediately adjacent cysteine and outside the motif a histidine or tryptophan is present, in other words the modified redox motif is written as [HW]-X(0,2)-C-X(2)-[CST] ([SEQ ID NO:1], [SEQ ID NO:2], [SEQ ID NO:3]) or [CST]-X(2)-C-X(0,2)-[HW] ([SEQ ID NO:4], [SEQ ID NO:5], [SEQ ID NO:6]).

Embodiments hereof are [HW]-X(2)-C-X(2)-[CST] [SEQ ID NO:3], [HW]-X-C-X(2)-[CST] [SEQ ID NO:2], [HW]-C-X(2)-[CST] [SEQ ID NO:1], [CST]-X(2)-C-X(2)-[HW] [SEQ ID NO:6], [CST]-X(2)-C-X-[HW] [SEQ ID NO:5], and [CST]-X(2)-C-[HW] [SEQ ID NO:4], More specific embodiments are:

| | |
|---|---|
| H-C-X(2)-S | [SEQ ID NO:18] |
| H-X-C-X(2)-S | [SEQ ID NO:19] |
| H-X(2)-C-X(2)-S | [SEQ ID NO:20] |
| W-C-X(2)-S | [SEQ ID NO:21] |
| W-X-C-X(2)-S | [SEQ ID NO:22] |
| W-X(2)-C-X(2)-S | [SEQ ID NO:23] |
| H-C-X(2)-T | [SEQ ID NO:24] |
| H-X-C-X(2)-T | [SEQ ID NO:25] |
| H-X(2)-C-X(2)-T | [SEQ ID NO:26] |
| W-C-X(2)-T | [SEQ ID NO:27] |
| W-X-C-X(2)-T | [SEQ ID NO:28] |
| W-X(2)-C-X(2)-T | [SEQ ID NO:29] |
| S-X(2)-C-H | [SEQ ID NO:30] |
| S-X(2)-C-X-H | [SEQ ID NO:31] |
| S-X(2)-C-X(2)-H | [SEQ ID NO:32] |
| S-X(2)-C-W | [SEQ ID NO:33] |
| S-X(2)-C-X-W | [SEQ ID NO:34] |
| S-X(2)-C-X(2)-W | [SEQ ID NO:35] |
| T-X(2)-C-H | [SEQ ID NO:36] |
| T-X(2)-C-X-H | [SEQ ID NO:37] |
| T-X(2)-C-X(2)-H | [SEQ ID NO:38] |
| T-X(2)-C-W | [SEQ ID NO:39] |
| T-X(2)-C-X-W | [SEQ ID NO:40] |
| T-X(2)-C-X(2)-W | [SEQ ID NO:41] |
| C-X(2)-C-H | [SEQ ID NO:42] |
| C-X(2)-C-X-H | [SEQ ID NO:43] |
| C-X(2)-C-X(2)-H | [SEQ ID NO:44] |
| C-X(2)-C-W | [SEQ ID NO:45] |
| C-X(2)-C-X-W | [SEQ ID NO:46] |
| C-X(2)-C-X(2)-W | [SEQ ID NO:47] |
| H-C-X(2)-C | [SEQ ID NO:48] |
| H-X-C-X(2)-C | [SEQ ID NO:49] |
| H-X(2)-C-X(2)-C | [SEQ ID NO:50] |
| W-C-X(2)-C | [SEQ ID NO:51] |
| W-X-C-X(2)-C | [SEQ ID NO:52] |
| W-X(2)-C-X(2)-C | [SEQ ID NO:53] |

In specific embodiments of the invention peptides with a [HW]-C-X(2)-C-[HW] [SEQ ID NO:67] motif are excluded from the scope of the invention.

Other specific embodiments are peptides wherein a cysteine amino acid of the redox motif is flanked by two histidine sequences such as HCHxC [SEQ ID NO:68].

Other specific embodiments are peptides wherein a cysteine amino acid of the redox motif is flanked by two tryptophan sequences such as WCWxC [SEQ ID NO:69].

As explained in detail further on, the peptides of the present invention can be made by chemical synthesis, which allows the incorporation of non-natural amino acids. Accordingly, "C" in the above recited redox modified redox motifs represents either cysteine or another amino acids with a thiol group such as mercaptovaline, homocysteine or other natural or non-natural amino acids with a thiol function. In order to have reducing activity, the cysteines present in a modified redox motif should not occur as part of a cysteine disulfide bridge. Nevertheless, a redox modified redox motif may comprise modified cysteines such as methylated cysteine, which is converted into cysteine with free thiol groups in vivo. X can be any of the 20 natural amino acids, including S, C, or T or can be a non-natural amino acid. In particular embodiments X is an amino acid with a small side chain such as Gly, Ala, Ser or Thr. In further particular embodiments, X is not an amino acid with a bulky side chain such as Trp. In further particular embodiments X is not cysteine. In further particular embodiments at least one X in the modified redox motif is His. In other further particular embodiments at least one X in the modified redox motif is Pro.

Peptides may further comprise modifications to increase stability or solubility, such as modification of the N-terminal $NH_2$ group or the C terminal COOH group (e.g. modification of the COOH into a $CONH_2$ group).

In the peptides of the present invention comprising a modified redox motif, the motif is located such that, when the epitope contains a redox motif sequence, the motif remains outside peptide binding part of the CD1d molecule. The modified redox motif is placed either immediately adjacent to the CD1d binding peptide epitope sequence within the peptide (in other words a linker sequence of zero amino acids between motif and epitope), or is separated from the CD1d binding peptide epitope by a linker comprising an amino acid sequence of 7 amino acids or less. More particularly, the linker comprises 1, 2, 3, or 4 amino acids. Specific embodiments are peptides with a 0, 1 or 2 amino acid linker between epitope sequence and modified redox motif sequence. Alternatively, a linker may comprise 5, 6, 7, 8, 9 or 10 amino acids. In those peptides where the modified redox motif sequence is adjacent to the epitope sequence this is indicated as position P−4 to P−1 or P+1 to P+4 compared to the epitope sequence. Apart from a peptide linker, other organic compounds can be used as linker to link the parts of the peptide to each other (e.g. the modified redox motif sequence to the CD1d binding peptide epitope sequence).

The peptides of the present invention can further comprise additional short amino acid sequences N or C-terminally of the sequence comprising the CD1d binding peptide epitope and the modified redox motif. Such an amino acid sequence is generally referred to herein as a 'flanking sequence'. A flanking sequence can be positioned between the epitope and an endosomal targeting sequence and/or between the modified redox motif and an endosomal targeting sequence. In certain peptides, not comprising an endosomal targeting sequence, a short amino acid sequence may be present N and/or C terminally of the modified redox motif and/or epitope sequence in the peptide. More particularly a flanking sequence is a sequence of between 1 and 7 amino acids, most particularly a sequence of 2 amino acids.

The modified redox motif may be located N-terminal from the epitope.

In certain embodiments, wherein the modified redox motif contains one cysteine, this cysteine is present in the modified redox motif in the position remote from the epitope, thus the modified redox motif occurs for example as W-C-X(2)-T [SEQ ID NO:27], H-C-X(2)-T [SEQ ID NO:24], H-C-X(2)-S [SEQ ID NO: 18], W-C-X(2)-S [SEQ ID NO:21] N-terminally of the epitope or occurs as T-X(2)-C-H [SEQ ID NO:36], T-X(2)-C-W [SEQ ID NO:39], S-X(2)-C-H [SEQ ID NO:30], S-X(2)-C-W [SEQ ID NO:33] C-terminally of the epitope.

In certain embodiments of the present invention, peptides are provided comprising one epitope sequence and a modified redox motif sequence. In further particular embodiments, the modified redox motif occurs several times (1, 2, 3, 4 or even more times) in the peptide, for example as repeats of the modified redox motif which can be spaced from each other by one or more amino acids or as repeats which are immediately adjacent to each other. Alternatively, one or more modified redox motifs are provided at both the N and the C terminus of the CD1d binding peptide epitope. Other variations envisaged for the peptides of the present invention include peptides which contain repeats of a CD1d binding peptide epitope sequence wherein each epitope sequence is preceded and/or followed by the modified redox motif (e.g. repeats of "modified redox motif-epitope" or repeats of "modified redox motif-epitope-modified redox motif"). Herein the modified redox motifs can all have the same sequence but this is not obligatory. It is noted that repetitive sequences of peptides which comprise an epitope which in itself comprises the modified redox motif will also result in a sequence comprising both the 'epitope' and a 'modified redox motif'. In such peptides, the modified redox motif within one epitope sequence functions as a modified redox motif outside a second epitope sequence.

Typically the peptides of the present invention comprise only one CD1d binding peptide. As described below a CD1d binding peptide in a protein sequence can be identified by scanning a protein sequence and has a length of 7 amino acids The CD1d binding peptide epitope of the peptides of the present invention can correspond either to a natural epitope sequence of a protein or can be a modified version thereof, provided the modified CD1d binding peptide epitope retains its ability to bind within the CD1d molecule, similar to the natural epitope sequence. The modified epitope can have the same binding affinity for the MHC protein as the natural epitope, but can also have a lowered affinity. In particular, the binding affinity of the modified peptide is no less than 10-fold less than the original peptide, more particularly no less than 5 times less. Peptides of the present invention have a stabilising effect on protein complexes. Accordingly, the stabilising effect of the peptide-CD1d complex compensates for the lowered affinity of the modified epitope for the CD1d molecule. The sequence comprising the CD1d binding peptide epitope and the reducing compound within the peptide can be further linked to an amino acid sequence (or another organic compound) that facilitates uptake of the peptide into late endosomes for processing and presentation. The late endosome targeting is mediated by signals present in the cytoplasmic tail of proteins and correspond to well-identified peptide motifs such as the dileucine-based [DE]XXXL[LI] [SEQ ID NO:70] or DXXLL [SEQ ID NO:71] motif, the tyrosine-based YXXϕ motif [SEQ ID NO:72] or the so called acidic cluster motif. The symbol ϕ represents amino acid residues with a bulky hydrophobic side chains such as Phe, Tyr and Trp. The late endosome targeting sequences allow for processing and efficient presentation. Such endosomal targeting sequences are contained, for example, within the gp75 protein (Vijayasaradhi et al. (1995) *J. Cell. Biol.* 130, 807-820), the human CD3 gamma protein, the HLA-BM 11 (Copier et al. (1996) *J. Immunol.* 157, 1017-1027), the cytoplasmic tail of the DEC205 receptor (Mahnke et al. (2000) *J. Cell Biol.* 151, 673-683). Other examples of peptides which function as sorting signals to the endosome are disclosed in the review of Bonifacio and Traub (2003) *Annu. Rev. Biochem.* 72, 395-447. The late endosome targeting sequence can be located either at the amino-terminal or at the carboxy-terminal end of the antigen derived peptide for efficient uptake and processing and can also be coupled through a flanking sequence, such as a peptide sequence of up to 10 amino acids.

Accordingly, the present invention envisages peptides of antigenic proteins and their use in eliciting specific immune reactions. These peptides can either correspond to fragments of proteins which comprise, within their sequence i.e. a reducing compound and a CD1d binding peptide epitope separated by at most 10, preferably 7 amino acids or less. Alternatively, and for most antigenic proteins, the peptides of the invention are generated by coupling a reducing compound, more particularly a reducing modified redox motif as described herein, N-terminally or C-terminally to a CD1d binding peptide epitope of the antigenic protein (either directly adjacent thereto or with a linker of at most 10, more particularly at most 7 amino acids). Moreover the CD1d binding peptide epitope sequence of the protein and/or the modified redox motif can be modified and/or one or more flanking sequences and/or a targeting sequence can be introduced (or modified), compared to the naturally occurring sequence. Thus, depending on whether or not the features of the present invention can be found within the sequence of the antigenic protein of interest, the peptides of the present invention can comprise a sequence which is 'artificial' or 'naturally occurring'.

The peptides of the present invention can vary substantially in length. The length of the peptides can vary from 12, i.e. consisting of a CD1d binding molecule of 7 amino acids, adjacent thereto the modified redox motif of 5 amino acids with the histidine or tryptophan, up to 20, 25, 30, 40, 50, 75, 100 or 200 amino acids. For example, a peptide may comprise an endosomal targeting sequence of 40 amino acids, a flanking sequence of about 2 amino acids, a motif as described herein of 5 amino acids, a linker of 4 amino acids and a CD1d binding peptide epitope of 7 amino acids. Accordingly, in particular embodiments, the complete peptides consist of between 12 amino acids up to 20, 30, 50, 75, 100 or 200 amino acids. More particularly, where the reducing compound is a modified redox motif as described herein, the length of the (artificial or natural) sequence comprising the epitope and modified redox motif optionally connected by a linker (referred to herein as 'epitope-modified redox motif' sequence), without the endosomal targeting sequence, is critical. The 'epitope-modified redox motif' more particularly has a length of 12, 13, 14, 15, 16, 17, 18 or 19 amino acids. Such peptides of 12 to 19 amino acids can optionally be coupled to an endosomal targeting signal of which the size is less critical.

As detailed above, in particular embodiments, the peptides of the present invention comprise a reducing modified redox motif as described herein linked to a CD1d binding peptide epitope sequence.

A small number of protein sequences, fragments of proteins or synthetic peptides may by coincidence comprise a modified redox motif sequence. However the chance that these proteins comprise a CD1d binding peptide epitope cell epitope in the proximity of the modified redox sequence becomes very small. If existing, such peptides will be probably known from epitope scanning experiments wherein sets of overlapping peptide fragments are synthesised. In such publications the interest goes to the CD1d binding and neglect the relevance of a modified redox motif with a histidine or tryptophan and the relevance of such peptides in medical applications. Such peptides are thus accidental disclosures unrelated to the inventive concept of the present invention.

In further particular embodiments, the peptides of the invention are peptides comprising CD1d binding peptide epitopes which do not comprise an amino acid sequence with redox properties within their natural sequence.

However, in alternative embodiments, the CD1d binding peptide epitope may comprise any sequence of amino acids ensuring the binding of the epitope to the CD1d molecule. Where an epitope of interest of an antigenic protein comprises a modified redox motif such as described herein within its epitope sequence, the immunogenic peptides according to the present invention comprise the sequence of a modified redox motif as described herein and/or of another reducing sequence coupled N- or C-terminally to the epitope sequence such that (contrary to the modified redox motif present within the epitope, which is buried within the cleft) the attached modified redox motif can ensure the reducing activity.

Accordingly the CD1d binding peptide epitope and motif are immediately adjacent or separated from each other and do not overlap. To assess the concept of "immediately adjacent" or "separated", the 7 amino acid sequence which binds to the CD1d molecule and has the above described CD1d binding motif is determined and the distance between this heptapeptide with the modified redox motif pentapeptide is determined.

Generally, the peptides of the present invention are not natural (thus no fragments of proteins as such) but artificial peptides which contain, in addition to a CD1d binding peptide epitope, a modified redox motif as described herein, whereby the modified redox motif is immediately separated from the epitope by a linker consisting of up to seven, most particularly up to four or up to 2 amino acids.

It has been shown that upon administration (i.e. injection) to a mammal of a peptide according to the invention (or a composition comprising such a peptide), the peptide elicits the activation of NKT cells recognising the antigen derived CD1d binding peptide epitope and provides an additional signal to the NKT cell through reduction a of surface receptor. This supra-optimal activation results in NKT cells acquiring cytolytic properties for the cell presenting the CD1d binding peptide epitope, as well as suppressive properties on bystander T cells. In this way, the peptides or composition comprising the peptides described in the present invention, which contain an antigen-derived CD1d binding peptide epitope and, outside the epitope, a modified redox motif can be used for direct immunisation of mammals, including human beings. The invention thus provides peptides of the invention or derivatives thereof, for use as a medicine. Accordingly, the present invention provides therapeutic methods which comprise administering one or more peptides according to the present invention to a patient in need thereof.

The present invention offers methods by which antigen-specific NKT cells endowed with cytolytic properties can be elicited by immunisation with small peptides.

The immunogenic properties of the peptides of the present invention are of particular interest in the treatment and prevention of immune reactions.

Peptides described herein are used as medicament, more particularly used for the manufacture of a medicament for the prevention or treatment of an immune disorder in a mammal, more in particular in a human.

The present invention describes methods of treatment or prevention of an immune disorder of a mammal in need for such treatment or prevention, by using the peptides of the invention, homologues or derivatives thereof, the methods comprising the step of administering to said mammal suffering from, or at risk of an immune disorder a therapeutically effective amount of the peptides of the invention, homologues or derivatives thereof such as to reduce the symptoms of the immune disorder or prevent the immune disorder affecting the individual. The treatment of both humans and animals, such as, pets and farm animals is envisaged. In an embodiment the mammal to be treated is a human. The immune disorders referred to above are in a particular embodiment selected from allergic diseases and autoimmune diseases. Allergic diseases are conventionally described as type-1 mediated diseases or IgE-mediated diseases. Clinical manifestations of allergic diseases include bronchial asthma, allergic rhinitis, atopic dermatitis, food hypersensitivity and anaphylactic reactions to insect bites or drugs. Allergic diseases are caused by hypersensitivity reactions of the immune system to specific substances called allergens (such as pollen, stings, drugs, or food). The most severe form of an allergic disorder is anaphylactic shock, which is a medical emergency. Allergens include airborne allergens, such as those of house dust mite, pets and pollens. Allergens also include ingested allergens responsible for food hypersensitivity, including fruits, vegetables and milk. In order to treat the above diseases, peptides according to the invention are generated from the antigenic proteins or allergens known or believed to be a causative factor of the disease. The allergens that can be used for selection of T-cell epitopes are typically allergens which are selected from the group consisting of: food allergens present in peanuts, fish e.g. codfish, egg white, crustacean e.g. shrimp, milk e.g. cow's milk, wheat, cereals, fruits of the Rosacea family (apple, plum, strawberry), vegetables of the Liliacea, Cruciferae, Solanaceae and Umbelliferae families, tree nuts, sesame, peanut, soybean and other legume family allergens, spices, melon, avocado, mango, fig, banana, . . . house dust mites allergens obtained from *Dermatophagoides* spp or *D.*

*pteronyssinus, D. farinae* and *D. microceras, Euroglyphus maynei* or *Blomia* sp., allergens from insects present in cockroach or Hymenoptera, allergens from pollen, especially pollens of tree, grass and weed, allergens from animals, especially in cat, dog, horse and rodent, allergens from fungi, especially from *Aspergillus, Alternaria* or *Cladosporium*, and occupational allergens present in products such as latex, amylase, etc.

The present invention further relates to peptides with the modified redox motif comprising CD1d binding peptides of viral proteins, which are encoded by the backbone of viral vectors, used in gene therapy and gene vaccination. The present invention further relates to methods of treatment or prevention of immunogenic response against a viral vector.

The present invention further relates to peptides with the modified redox motif comprising CD1d binding peptides of proteins of intracellular pathogens. The present invention further relates to methods of treatment and prevention of infections with intracellular pathogens. Examples of intracellular pathogens (viruses such as DNA vs RNA viruses, single stranded vs double stranded viruses, bacteria, mycobacteria or parasites with an intracellular life cycle, and antigens that are discussed in WO2009101208 (for example Herpesviridae, Flaviviridae and Picornaviridae, influenza, measles and immunodeficiency viruses, papilloviruses). Examples of intracellular pathogens also includes bacteria and mycobacteria including *Mycobacterium tuberculosis*, and other mycobacteria pathogenic for humans or animals such as Yersiniae, Brucellae, Chlamydiae, Mycoplasmae, Rickettsiae, Salmonellae and Shigellae. Further examples include parasites such as Plasmodiums, Leishmanias, Trypanosomas, *Toxoplasma gondii, Listeria* sp., *Histoplasma* sp.

The present invention further relates to peptides with the modified redox motif comprising CD1d binding peptides of soluble allofactors such as used in replacement therapies. The present invention further relates to methods of treatment and prevention of immune reactions against soluble allofactors. Examples of soluble allofactors are disclosed in WO2009101206.

The present invention further relates to peptides with the modified redox motif comprising CD1d binding peptides of tumour associated antigens. The present invention further relates to methods of treatment and prevention of tumours. Examples of relevant tumours (e.g. oncogene, proto-oncogene, viral protein, a surviving factor, clonotypic determinant) and tumour associated antigens are disclosed in WO WO2009101205. Such tumor associated antigens include viral antigens of tumour causing viruses such as HPV, tumour associated antigens of a patient which have a wild-type sequence but have an increased expression in tumours, or antigens which have a mutated sequence by point mutations, deletions, frame shifts, or chromosomal rearrangements.

The present invention further relates to peptides with the modified redox motif comprising CD1d binding peptides of alloantigenic protein of an allograft. The present invention further relates to methods of treatment and prevention of allograft rejection. Examples are bone marrow grafts, solid organ grafts such as kidney, lung, heart, liver, pancreas, bone or skin, or cellular grafts such as cord blood cell graft, stem cell graft, or pancreatic islet cell grafts. Examples of alloantigenic proteins are disclosed in WO2009100505, such as minor histocompatibility antigens, major histocompatibility antigens or tissue-specific antigens.

For all the above peptides additional variant are envisaged, wherein between histidine or tryptophan and cysteine, one or two amino acids X are present. Typically these external amino acid(s) X is (are) not His, Trp, Cys, Ser or Thr.

The peptides of the present invention can also be used in diagnostic in vitro methods for detecting CD1d positive cells in a sample. In this method a sample is contacted with a complex of a CD1d molecule and a peptide according to the present invention. The CD1d cells are detected by measuring the binding of the complex with cells in the sample, wherein the binding of the complex to a cell is indicative for the presence of CD1d positive cells in the sample.

The complex can be a fusion protein of the peptide and an MHC class II molecule. Alternatively MHC molecules in the complex are tetramers. The complex can be provided as a soluble molecule or can be attached to a carrier.

The CD1d binding peptide corresponding to an antigenic protein (or immunogen) suitable for use in the context of the present invention can be of an airborne allergen or a food-borne allergen. In particular embodiments, the allergen is selected from the group consisting of rhino-sinusitis allergens, allergic bronchial asthma allergens and atopic dermatitis allergens. Allergens can also be main allergens present in moulds or various drugs such as hormones, antibiotics, enzymes, etc. (See also the definition in *Clin. Exp. Allergy* 26, 494-516 (1996) and in Molecular Biology of Allergy and Immunology, Ed. R. Bush (1996)). Other allergens related to specific allergic diseases are also well known in the art and can be found on the internet, e.g. on allergome.org. Auto-immune diseases are broadly classified into two categories, organ-specific and systemic diseases. The precise aetiology of systemic auto-immune diseases is not identified. In contrast, organ-specific auto-immune diseases are related to a specific immune response including B and T cells, which targets the organ and thereby induces and maintains a chronic state of local inflammation. Examples of organ-specific auto-immune diseases include type 1 diabetes, myasthenia gravis, thyroiditis and multiple sclerosis. In each of these conditions, a single or a small number of auto-antigens has been identified, including insulin, the acetyl-choline muscle receptor, thyroid peroxidase and major basic protein, respectively. It is well recognised that suppression of this organ-specific immune response is beneficial and leads to partial or complete recovery of organ function. There is, however, no therapy, which would suppress such an immune response in an antigen-specific manner. Current therapy rather makes use of non-specific suppression obtained by the use of corticosteroids and immunosuppressive agents, all exhibiting significant side-effects related to their absence of specificity, thereby limiting their use and their overall efficacy. A non-limiting list of examples of organ specific autoimmune disorders and auto-antigens involved therein which are envisaged within the context of the present invention are:

thyroid diseases: thyroglobulin, thyroid peroxidase, TSH receptor type 1 diabetes: insulin (proinsulin), glutamic acid decarboxylase (GAD), tyrosine phosphatase IA-2, heat-shock protein HSP65, islet-specific glucose6-phosphatase catalytic subunit related protein (IGRP)

Adrenalitis: 21-OH hydroxylase polyendocrine syndromes: 17-alpha hydroxylase, histidine decarboxylase, tryptophan hydroxylase, tyrosine hydroxylase gastritis & pernicious anemia: H+/K+ ATPase intrinsic factor multiple sclerosis: myelin oligodendrocyte glycoprotein (MOG), myelin basic protein (MBP), proteolipid (PLP)

myasthenia gravis: acetyl-choline receptor
ocular diseases: retinol-binding protein (RBP)
inner ear diseases: type II and type IX collagen
celiac disease: tissue transglutaminase
inflammatory bowel diseases: pANCA histone H1 protein
Atherosclerosis: heat-shock protein HSP60

According to the present invention, immunogenic peptides are provided which comprise a CD1d binding peptide epitope of an antigen (self or non-self) with a potential to trigger an immune reaction.

Accordingly, in particular embodiments, the methods of treatment and prevention of the present invention comprise the administration of an immunogenic peptide as described herein, wherein the peptide comprise a CD1d binding peptide epitope of an antigenic protein which plays a role in the disease to be treated (for instance such as those described above).

The present invention further relates to methods to produce peptides with a CD1d binding peptide epitope and a modified redox motif.

In a first step the method comprises the step of providing the sequence of an antigenic protein of interest and identifying a CD1d binding peptide sequence in the antigen using the above cited peptide motifs for a CD1d binding peptide.

Such epitope sequences may have been described yet for the antigenic protein under consideration. Alternatively they are determined by in silico methods, in vitro methods or in vivo methods. In addition the antigenic protein is screened for the presence of the modified redox motif, which requires no specific in silico methods. There is a very small, but existing, chance that an antigenic protein contains within its sequence a [HW]-X(0,2)-C-X(2)-[CST] ([SEQ ID NO:1], [SEQ ID NO:2], [SEQ ID NO:3]) or [CST]-X(2)-C-X(0,2)-[HW] ([SEQ ID NO:4], [SEQ ID NO:5], [SEQ ID NO:6]) motif in the close proximity of a CD1d binding peptide epitope sequence (i.e. separated from the CD1d binding peptide epitope by 7 or fewer amino acids). If so, a fragment of the antigenic protein comprising CD1d binding peptide epitope and motif can be used for the methods and uses of the present invention. The epitope in such proteins may have been discussed in the prior art but the presence, let alone, the relevance of such modified redox motif has not been discussed. There has been accordingly no incentive in the prior art to select such peptide fragments, or to use such peptide fragments for the methods described herein. In certain embodiments, wherein the peptide is based on a fragment of a protein which contains an CD1d binding peptide and a modified redox motif such a peptide sequence may be further modified by changing the length of the sequence between the epitope and the modified redox motif, changing amino acids in the linker sequence, changing a Ser or Thr in the motif into a cysteine or changing amino acids at one or both X positions within the motif.

Other antigenic proteins which are used for the design of peptides may contain a [HW]-X(0,2)-C-X(2)-[CST] ([SEQ ID NO:1], [SEQ ID NO:2], [SEQ ID NO:3]) or [CST]-X(2)-C-X(0,2)-[HW] ([SEQ ID NO:4], [SEQ ID NO:5], [SEQ ID NO:6]) sequence in its sequence which is further remote from a CD1d binding peptide (more than 7 amino acids from the epitope sequence).

In such cases a peptide can be produced wherein only the distance between the epitope and the motif is shortened and whereby the sequence of the motif and neighbouring amino acids are preserved. If deemed suitable, amino acids outside the motif, serine or threonine in the motif or one or both X positions are changed. Generally, antigenic proteins which are used for the design of peptides will not contain a [HW]-X(0,2)-C-X(2)-[CST] ([SEQ ID NO:1], [SEQ ID NO:2], [SEQ ID NO:3]) or [CST]-X(2)-C-X(0,2)-[HW] ([SEQ ID NO:4], [SEQ ID NO:5], [SEQ ID NO:6]) sequence within their protein sequence. Peptides in accordance with the present invention will be prepared by synthesising a peptide wherein CD1d binding peptide epitope and modified redox motif will be separated by 0 to 7 amino acids. In certain embodiments the modified redox motif can be obtained by introducing 1, 2 or 3 mutations outside the epitope sequence, to preserve the sequence context as occurring in the protein. In other embodiments the sequence N terminal or C terminal of the epitope will be unrelated to the sequence of the antigenic protein containing the CD1d binding peptide epitope sequence.

In other specific embodiments, peptides are prepared by modifying peptides with a CD1d binding peptide epitope and a C-X(2)-[CST] [SEQ ID NO:55] or [CST]-X(2)-C [SEQ ID NO:54] motif as disclosed in WO2012069568. Addition of a histidine or tryptophan or modification of an amino acid into a histidine or tryptophan leads to peptides of the present invention with a [HW]-X(0,2)-C-X(2)-[CST] ([SEQ ID NO:4], [SEQ ID NO:5], [SEQ ID NO:6]) or [CST]-X(2)-C-X(0,2)-[HW] ([SEQ ID NO:4], [SEQ ID NO:5], [SEQ ID NO:6]) sequence.

Thus based upon the above methods for designing a peptide, a peptide is generated by chemical peptide synthesis, recombinant expression methods or in more exceptional cases, proteolytic or chemical fragmentation of proteins.

Peptides as produced in the above methods can be tested for CD1d binding in in vitro and in vivo methods, and can be tested for their reducing activity in in vitro assays.

As a final quality control, the peptides can be tested in in vitro assays to verify whether the peptides can generate NKT cells which are cytolytic via an apoptotic pathway for antigen presenting cells presenting the antigen which contains the epitope sequence which is also present in the peptide with the modified redox motif.

As explained before peptides may comprise exceptionally in their sequence both a CD1d binding peptide epitope and a MHC class II epitope. Such peptides are excluded from the present invention and methods to identify T cell epitopes are disclosed herein. The identification and selection of a T-cell epitope from antigenic proteins is known to a person skilled in the art.

To identify an epitope, isolated peptide sequences of an antigenic protein are tested by, for example, T cell biology techniques, to determine whether the peptide sequences elicit a T cell response. Those peptide sequences found to elicit a T cell response are defined as having T cell stimulating activity.

Human T cell stimulating activity can further be tested by culturing T cells obtained from an individual sensitive to e.g. a mite allergen, (i.e. an individual who has an IgE mediated immune response to a mite allergen) with a peptide/epitope derived from the allergen and determining whether proliferation of T cells occurs in response to the peptide/epitope as measured, e.g., by cellular uptake of tritiated thymidine. Stimulation indices for responses by T cells to peptides/epitopes can be calculated as the maximum CPM in response to a peptide/epitope divided by the control CPM. A T cell stimulation index (S.I.) equal to or greater than two times the background level is considered "positive". Positive results are used to calculate the mean stimulation index for each peptide/epitope for the group of peptides/epitopes tested.

Non-natural (or modified) T-cell epitopes can further optionally be tested on their binding affinity to MHC class II molecules. This can be performed in different ways. For instance, soluble HLA class II molecules are obtained by lysis of cells homozygous for a given class II molecule. The latter is purified by affinity chromatography. Soluble class II molecules are incubated with a biotin-labelled reference peptide produced according to its strong binding affinity for that class II molecule. Peptides to be assessed for class II binding are then incubated at different concentrations and their capacity to displace the reference peptide from its class II binding is calculated by addition of neutravidin. Methods can be found in for instance Texier et al., (2000) *J. Immunology* 164, 3177-3184.)

In order to determine optimal T cell epitopes by, for example, fine mapping techniques, a peptide having T cell stimulating activity and thus comprising at least one T cell epitope as determined by T cell biology techniques is modified by addition or deletion of amino acid residues at either the amino- or carboxyterminus of the peptide and tested to determine a change in T cell reactivity to the modified peptide. If two or more peptides which share an area of overlap in the native protein sequence are found to have human T cell stimulating activity, as determined by T cell biology techniques, additional peptides can be produced comprising all or a portion of such peptides and these additional peptides can be tested by a similar procedure. Following this technique, peptides are selected and produced recombinantly or synthetically. T cell epitopes or peptides are selected based on various factors, including the strength of the T cell response to the peptide/epitope (e.g., stimulation index) and the frequency of the T cell response to the peptide in a population of individuals.

Additionally and/or alternatively, one or more in vitro algorithms can be used to identify a T cell epitope sequence within an antigenic protein. Suitable algorithms include, but are not limited to those described in Zhang et al. (2005) *Nucleic Acids Res* 33, W180-W183 (PREDBALB); Salomon & Flower (2006) *BMC Bioinformatics* 7, 501 (MHCBN); Schuler et al. (2007) *Methods Mol. Biol.* 409, 75-93 (SYFPEITHI); Donnes & Kohlbacher (2006) *Nucleic Acids Res.* 34, W194-W197 (SVMHC); Kolaskar & Tongaonkar (1990) *FEBS Lett.* 276, 172-174, Guan et al. (2003) *Appl. Bioinformatics* 2, 63-66 (MHCPred) and Singh and Raghava (2001) *Bioinformatics* 17, 1236-1237 (Propred).

More particularly, such algorithms allow the prediction within an antigenic protein of one or more octa- or nonapeptide sequences which will fit into the groove of an MHC II molecule and this for different HLA types.

The peptides of the present invention can be generated using recombinant DNA techniques, in bacteria, yeast, insect cells, plant cells or mammalian cells. In view of the limited length of the peptides, they can be prepared by chemical peptide synthesis, wherein peptides are prepared by coupling the different amino acids to each other. Chemical synthesis is particularly suitable for the inclusion of e.g. D-amino acids, amino acids with non-naturally occurring side chains or natural amino acids with modified side chains such as methylated cysteine.

Chemical peptide synthesis methods are well described and peptides can be ordered from companies such as Applied Biosystems and other companies.

Peptide synthesis can be performed as either solid phase peptide synthesis (SPPS) or contrary to solution phase peptide synthesis. The best-known SPPS methods are t-Boc and Fmoc solid phase chemistry.

During peptide synthesis several protecting groups are used. For example hydroxyl and carboxyl functionalities are protected by t-butyl group, lysine and tryptophan are protected by t-Boc group, and asparagine, glutamine, cysteine and histidine are protected by trityl group, and arginine is protected by the pbf group. If appropriate, such protecting groups can be left on the peptide after synthesis. Peptides can be linked to each other to form longer peptides using a ligation strategy (chemoselective coupling of two unprotected peptide fragments) as originally described by Kent (Schnelzer & Kent (1992) *Int. J. Pept. Protein Res.* 40, 180-193) and reviewed for example in Tam et al. (2001) *Biopolymers* 60, 194-205 provides the tremendous potential to achieve protein synthesis which is beyond the scope of SPPS. Many proteins with the size of 100-300 residues have been synthesised successfully by this method. Synthetic peptides have continued to play an ever increasing crucial role in the research fields of biochemistry, pharmacology, neurobiology, enzymology and molecular biology because of the enormous advances in the SPPS.

Alternatively, the peptides can be synthesised by using nucleic acid molecules which encode the peptides of this invention in an appropriate expression vector which include the encoding nucleotide sequences. Such DNA molecules may be readily prepared using an automated DNA synthesiser and the well-known codon-amino acid relationship of the genetic code. Such a DNA molecule also may be obtained as genomic DNA or as cDNA using oligonucleotide probes and conventional hybridisation methodologies. Such DNA molecules may be incorporated into expression vectors, including plasmids, which are adapted for the expression of the DNA and production of the polypeptide in a suitable host such as bacterium, e.g. *Escherichia coli*, yeast cell, animal cell or plant cell.

The physical and chemical properties of a peptide of interest (e.g. solubility, stability) are examined to determine whether the peptide is/would be suitable for use in therapeutic compositions. Typically this is optimised by adjusting the sequence of the peptide. Optionally, the peptide can be modified after synthesis (chemical modifications e.g. adding/deleting functional groups) using techniques known in the art.

The present invention provides methods for generating antigen-specific cytolytic NKT cells either in vivo or in vitro and, independently thereof, and methods to discriminate NKT cells from other cell populations such as Foxp3+ Tregs based on characteristic expression data.

The present invention describes in vivo methods for the production of the antigen-specific NKT cells. A particular embodiment relates to the method for producing or isolating the NKT cells by immunising animals (including humans) with the peptides of the invention as described herein and then isolating the NKT cells from the immunised animals. The present invention describes in vitro methods for the production of antigen specific cytolytic NKT cells towards APC. The present invention provides methods for generating antigen specific cytolytic NKT cells towards APC.

In one embodiment, methods are provided which comprise the isolation of peripheral blood cells, the stimulation of the cell population in vitro by an immunogenic peptide according to the invention and the expansion of the stimulated cell population, more particularly in the presence of cytokines of the gamma chain family. The methods according to the invention have the advantage a high number of NKT cells is produced and that the NKT cells can be generated which are specific for the antigenic protein (by using a peptide comprising an antigen-specific epitope).

In an alternative embodiment, the NKT cells can be generated in vivo, i.e. by the injection of the immunogenic peptides described herein to a subject, and collection of the cytolytic NKT cells generated in vivo.

The antigen-specific cytolytic NKT cells towards APC, obtainable by the methods of the present invention are of particular interest for the administration to mammals for immunotherapy, in the prevention of allergic reactions and the treatment of auto-immune diseases. Both the use of allogenic and autogeneic cells are envisaged. Antigen-specific cytolytic NKT cells as described herein can be used as a medicament, more particularly for use in adoptive cell therapy, more particularly in the treatment of acute allergic reactions and relapses of autoimmune diseases such as multiple sclerosis. Isolated cytolytic NKT cells or cell populations, more particularly antigen-specific cytolytic NKT cell populations generated as described are used for the manufacture of a medicament for the prevention or treatment of immune disorders. Methods of treatment by using the isolated or generated cytolytic NKT cells are disclosed.

This mechanism also implies and the experimental results show that the peptides of the invention, although comprising a specific CD1d binding peptide epitope of a certain antigen, can be used for the prevention or treatment of disorders elicited by an immune reaction against other CD1d binding peptide epitopes of the same antigen or in certain circumstances even for the treatment of disorders elicited by an immune reaction against other CD1d binding peptide epitope of other different antigens if they would be presented through the same mechanism by CD1d molecules in the vicinity of T cells activated by peptides of the invention.

Isolated cell populations of the cell type having the characteristics described above, which, in addition are antigen-specific (i.e. capable of suppressing an antigen-specific immune response) are disclosed.

The peptides of the invention may also be used in gene therapy methods well known in the art and the terminology used herein explaining the use of peptides according to the invention also includes the use of nucleic acids encoding or expressing immunogenic peptides according to the invention.

The present invention describes nucleic acid sequences encoding the peptides of the present invention and methods for their use. Different methods of achieving, by way of gene therapy, levels of peptides, homologues or derivatives thereof according to the invention in a mammal in vivo are envisaged within the context of the present invention.

Recombinant nucleic acid molecules encoding protein sequences can be used as naked DNA or in liposomes or other lipid systems for delivery to target cells. Other methods for the direct transfer of plasmid DNA into cells are well known to those skilled in the art for use in human gene therapy and involve targeting the DNA to receptors on cells by complexing the plasmid DNA to proteins. In its simplest form, gene transfer can be performed by simply injecting minute amounts of DNA into the nucleus of a cell, through a process of microinjection. Once recombinant genes are introduced into a cell, they can be recognised by the cells normal mechanisms for transcription and translation, and a gene product will be expressed. Other methods have also been attempted for introducing DNA into larger numbers of cells. These methods include: transfection, wherein DNA is precipitated with calcium phosphate and taken into cells by pinocytosis; electroporation, wherein cells are exposed to large voltage pulses to introduce holes into the membrane); lipofection/liposome fusion, wherein DNA is packed into lipophilic vesicles which fuse with a target cell; and particle bombardment using DNA bound to small projectiles. Another method for introducing DNA into cells is to couple the DNA to chemically modified proteins. Adenovirus proteins are capable of destabilising endosomes and enhancing the uptake of DNA into cells. Mixing adenovirus to solutions containing DNA complexes, or the binding of DNA to polylysine covalently attached to adenovirus using protein crosslinking agents substantially improves the uptake and expression of the recombinant gene. Adeno-associated virus vectors may also be used for gene delivery into vascular cells. As used herein, "gene transfer" means the process of introducing a foreign nucleic acid molecule into a cell, which is commonly performed to enable the expression of a particular product encoded by the gene. The product may include a protein, polypeptide, anti-sense DNA or RNA, or enzymatically active RNA. Gene transfer can be performed in cultured cells or by direct administration into mammals. In another embodiment, a vector comprising a nucleic acid molecule sequence encoding a peptide according to the invention is provided. In particular embodiments, the vector is generated such that the nucleic acid molecule sequence is expressed only in a specific tissue. Methods of achieving tissue-specific gene expression are well known in the art. This can be for example achieved by placing the sequence encoding a peptide according to the invention under control of a promoter which directs expression in one or more particular tissues.

Expression vectors derived from viruses such as retroviruses, vaccinia virus, adenovirus, adeno-associated virus, herpes viruses, RNA viruses or bovine papilloma virus, may be used for delivery of nucleotide sequences (e.g., cDNA) encoding peptides, homologues or derivatives thereof according to the invention into the targeted tissues or cell population. Methods which are well known to those skilled in the art can be used to construct recombinant viral vectors containing such coding sequences.

Accordingly, the present invention discloses the use of a nucleic acid which is capable of expressing the peptides of the invention, in vivo, for the treatment and/or prevention of diseases driven by an immune response to a foreign or selfantigen. According to one embodiment, the nucleic acid capable of expressing a peptide according to the invention in vivo is a sequence encoding such a peptide, which is operably linked to a promoter. Such a sequence can be administered directly or indirectly. For instance, an expression vector containing the coding sequence for a peptide according to the invention may be inserted into cells, after which the cells are grown in vitro and then injected or infused into the patient. Alternatively the nucleic acid capable of expressing a peptide according to the invention in vivo is a sequence which modifies endogenous expression of the cells. The gene therapy method may involve the use of an adenovirus vector including a nucleotide sequence coding for peptides, homologues or derivatives thereof according to the invention or a naked nucleic acid molecule coding for a peptide according to the invention. Alternatively, engineered cells containing a nucleic acid molecule coding for a peptide according to the invention may be injected.

Where the administration of one or more peptides according to the invention is ensured through gene transfer (i.e. the administration of a nucleic acid which ensures expression of peptides according to the invention in vivo upon administration), the appropriate dosage of the nucleic acid can be determined based on the amount of peptide expressed as a result of the nucleic acid, such as e.g. by determining the concentration of peptide in the blood after administration. Thus, in a particular embodiment, the peptides of the invention are administered through the use of polynucleotides encoding the peptides, whether in an expression vector or not and thus the present invention also relates to gene therapy methods. Another particular embodiment relates to the use of methods to induce a local overexpression of the peptides of the invention for the treatment or prevention of immune disorders.

The present invention provides pharmaceutical compositions comprising one or more peptides according to the present invention, further comprising a pharmaceutically acceptable carrier. As detailed above, the present invention also relates to the compositions for use as a medicine or to methods of treating a mammal of an immune disorder by using the composition and to the use of the compositions for the manufacture of a medicament for the prevention or treatment of immune disorders. The pharmaceutical composition could for example be a vaccine suitable for treating or preventing immune disorders, for example airborne and foodborne allergy, as well as diseases of allergic origin. As an example described further herein of a pharmaceutical composition, a peptide according to the invention is adsorbed on an adjuvant suitable for administration to mammals, such as aluminium hydroxide (alum). Typically, 50 μg of the peptide adsorbed on alum are injected by the subcutaneous route on 3 occasions at an interval of 2 weeks. It should be obvious for those skilled in the art that other routes of administration are possible, including oral, intranasal or intramuscular. Also, the number of injections and the amount injected can vary depending on the conditions to be treated. Further, other adjuvants than alum can be used, provided they facilitate peptide presentation CD1d presentation and T cell activation. Thus, while it is possible for the active ingredients to be administered alone, they typically are presented as pharmaceutical formulations. The formulations, both for veterinary and for human use, of the present invention comprise at least one active ingredient, as above described, together optionally with one or more pharmaceutically acceptable carriers. The present invention relates to pharmaceutical compositions, comprising, as an active ingredient, one or more peptides according to the invention, in admixture with a pharmaceutically acceptable carrier. The pharmaceutical composition of the present invention should comprise a therapeutically effective amount of the active ingredient, such as indicated hereinafter in respect to the method of treatment or prevention. Optionally, the composition further comprises other therapeutic ingredients. Suitable other therapeutic ingredients, as well as their usual dosage depending on the class to which they belong, are well known to those skilled in the art and can be selected from other known drugs used to treat immune disorders.

The term "pharmaceutically acceptable carrier" as used herein means any material or substance with which the active ingredient is formulated in order to facilitate its application or dissemination to the locus to be treated, for instance by dissolving, dispersing or diffusing the composition, and/or to facilitate its storage, transport or handling without impairing its effectiveness. They include any and all solvents, dispersion media, coatings, antibacterial and antifungal agents (for example phenol, sorbic acid, chlorobutanol), isotonic agents (such as sugars or sodium chloride) and the like. Additional ingredients may be included in order to control the duration of action of the immunogenic peptide in the composition. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, suspensions, ointments, creams, tablets, pellets or powders. Suitable pharmaceutical carriers for use in the pharmaceutical compositions and their formulation are well known to those skilled in the art, and there is no particular restriction to their selection within the present invention. They may also include additives such as wetting agents, dispersing agents, stickers, adhesives, emulsifying agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals. The pharmaceutical compositions of the present invention may be prepared in any known manner, for instance by homogeneously mixing, coating and/or grinding the active ingredients, in a one-step or multi-steps procedure, with the selected carrier material and, where appropriate, the other additives such as surface-active agents. They may also be prepared by micronisation, for instance in view to obtain them in the form of microspheres usually having a diameter of about 1 to 10 μm, namely for the manufacture of microcapsules for controlled or sustained release of the active ingredients.

Suitable surface-active agents, also known as emulgent or emulsifier, to be used in the pharmaceutical compositions of the present invention are non-ionic, cationic and/or anionic materials having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids (C10-C22), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives typically contain 8 to 22 carbon atoms. Examples of alkylarylsulphonates are the sodium, calcium or alcanolamine salts of dodecyl benzene sulphonic acid or dibutyl-naphtalenesulphonic acid or a naphtalene-sulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardio-lipin, dioctanylphosphatidylcholine, dipalmitoylphoshatidylcholine and their mixtures.

Suitable non-ionic surfactants include polyethoxylated and poly-propoxylated derivatives of alkyl phenols, fatty alcohols, fatty acids, aliphatic amines or amides containing at least 12 carbon atoms in the molecule, alkylarene sulphonates and dialkylsulphosuccinates, such as polyglycol ether derivatives of aliphatic and cycloaliphatic alcohols, saturated and unsaturated fatty acids and alkylphenols, the derivatives typically containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylenediaminopolypropylene glycol containing 1 to 10 carbon atoms in the alkyl chain, which adducts contain 20 to 250 ethyleneglycol ether groups and/or 10 to 100 propyleneglycol ether groups. Such compounds usually contain from I to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants. Suitable cationic surfactants include quaternary ammonium salts, particularly halides, having 4 hydrocarbon radicals optionally substituted with halo, phenyl, substituted phenyl or hydroxy; for instance quaternary ammonium salts containing as N-substituent at least one C8C22 alkyl radical (e.g. cetyl, lauryl, palmityl, myristyl, oleyl and the like) and, as further substituents, unsubstituted or halogenated lower alkyl, benzyl and/or hydroxy-lower alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbucw', 2 d ed. (Hanser Verlag, Vienna, 1981) and "Encyclopedia of Surfactants, (Chemical Publishing Co., New York, 1981). Peptides, homologues or derivatives thereof according to the invention (and their physiologically acceptable salts or pharmaceutical compositions all included in the term "active ingredients") may be administered by any route appropriate to the condition to be treated and appropriate for the compounds, here the proteins and fragments to be administered. Possible routes include regional, systemic, oral (solid form or inhalation), rectal, nasal, topical (including ocular, buccal and sublingual), vaginal and parenteral (including subcutaneous, intramuscular, intravenous, intradermal, intra-arterial, intrathecal and epidural). The preferred route of administration may vary with for example the condition of the recipient or with the diseases to be treated. As described herein, the carrier(s) optimally are "acceptable" in the sense of being compatible with the other ingredients of the formulation and not deleterious to the recipient thereof. The formulations include those suitable for oral, rectal, nasal, topical (including buccal and sublingual), vaginal or parenteral (including subcutaneous, intramuscular, intravenous, intradermal, intraarterial, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product. Formulations of the present invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste. A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

For local treatments for example on the skin, such as of the joint, the formulations are optionally applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), particularly 0.2 to 15% w/w and more particularly 0.5 to 10% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG400) and mixtures thereof. The topical formulations may desirably include a compound which enhances absorption or penetration of the active ingredient through the skin or other affected areas. Examples of such dermal penetration enhancers include dimethylsulfoxide and related analogues. The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Optionally, a hydrophilic emulsifier is included together with a lipophilic emulsifier, which acts as a stabiliser, typically by including both an oil and a fat. Together, the emulsifier(s) with or without stabiliser(s) make up the so-called emulsifying wax, and the wax together with the oil and fat make up the so-called emulsifying ointment base which forms the oily dispersed phase of the cream formulations.

The choice of suitable oils or fats for the formulation is based on achieving the desired cosmetic properties, since the solubility of the active compound in most oils likely to be used in pharmaceutical emulsion formulations is very low. Thus the cream should optionally be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, and particularly butyl stearate, 2-ethylhexyl palmitate or a blend of branched chain esters known as Crodamol CAP may be used. These may be used alone or in combination depending on the properties required. Alternatively, high melting point lipids such as white soft paraffin and/or liquid paraffin or other mineral oils can be used. Formulations suitable for topical administration to the eye also include eye drops wherein the active ingredient is dissolved or suspended in a suitable carrier, especially an aqueous solvent for the active ingredient. The active ingredient is optionally present in such formulations in a concentration of 0.5 to 20%, advantageously 0.5 to 10% particularly about 1.5% w/w. Formulations suitable for topical administration in the mouth include lozenges comprising the active ingredient in a flavoured basis, usually sucrose and acacia or tragacanth; pastilles comprising the active ingredient in an inert basis such as gelatin and glycerine, or sucrose and acacia; and mouthwashes comprising the active ingredient in a suitable liquid carrier. Formulations for rectal administration may be presented as a suppository with a suitable base comprising for example cocoa butter or a salicylate. Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc), which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents. Formulations suitable for vaginal administration may be presented as pessaries, tampons, creams, gels, pastes, foams or spray formulations containing in addition to the active ingredient such carriers as are known in the art to be appropriate. Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Typical unit dosage formulations are those containing a daily dose or unit daily sub-dose, as herein above recited, or an appropriate fraction thereof, of an active ingredient. It should be understood that in addition to the ingredients particularly mentioned above the formulations of this invention may include other agents conventional in the art having regard to the type of formulation in question, for example those suitable for oral administration may include flavouring agents. Peptides, homologues or derivatives thereof according to the invention can be used to provide controlled release pharmaceutical formulations containing as active ingredient one or more compounds of the invention ("controlled release formulations") in which the release of the active ingredient can be controlled and regulated to allow less frequency dosing or to improve the pharmacokinetic or toxicity profile of a given invention compound. Controlled release formulations adapted for oral administration in which discrete units comprising one or more compounds of the invention can be prepared according to conventional methods. Additional ingredients may be included in order to control the duration of action of the active ingredient in the composition. Control release compositions may thus be achieved by selecting appropriate polymer carriers such as for example polyesters, polyamino acids, polyvinyl pyrrolidone, ethylene-vinyl acetate copolymers, methylcellulose, carboxymethylcellulose, protamine sulfate and the like. The rate of drug release and duration of action may also be controlled by incorporating the active ingredient into particles, e.g. microcapsules, of a polymeric substance such as hydrogels, polylactic acid, hydroxymethylcellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition may require protective coatings. Pharmaceutical forms suitable for injection include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol and the like and mixtures thereof. In view of the fact that, when several active ingredients are used in combination, they do not necessarily bring out their joint therapeutic effect directly at the same time in the mammal to be treated, the corresponding composition may also be in the form of a medical kit or package containing the two ingredients in separate but adjacent repositories or compartments. In the latter context, each active ingredient may therefore be formulated in a way suitable for an administration route different from that of the other ingredient, e.g. one of them may be in the form of an oral or parenteral formulation whereas the other is in the form of an ampoule for intravenous injection or an aerosol.

Cytolytic NKT cells as obtained in the present invention, induce APC apoptosis after CD1d dependent cognate activation, affecting both dendritic and B cells, as demonstrated in vitro and in vivo, and suppress bystander T cells by a contact-dependent mechanism in the absence of IL-10 and/or TGF-beta. Cytolytic NKT cells can be distinguished from both natural and adaptive Tregs, as discussed in WO 2012/069568

The present invention will now be illustrated by means of the following examples which are provided without any limiting intention. Furthermore, all references described herein are explicitly included herein by reference.

EXAMPLES

Example 1: Methodology to Assess Reducing Activity of Peptides

The reductase activity of the peptides is determined using a fluorescent described in Tomazzolli et al. (2006) *Anal. Biochem.* 350, 105-112. Two peptides with a FITC label become self-quenching when they covalently attached to each other via a disulfide bridge. Upon reduction by a peptide in accordance with the present invention, the reduced individual peptides become fluorescent again.

Control experiments were performed with a peptide with a "normal" reducing peptide, i.e. a peptide with a redox motif but without additional histidine or tryptophan and with a peptide comprising no redox motif.

In practice a FITC-NH-Gly-Cys-Asp-COOH peptide was synthesized (Eurogentec, Belgium) and self-quenched by solubilization in DMSO ((FITC-Gly-Cys-Asp)$_{ox}$). The reduction of 2.5 µM (FITC-Gly-Cys-Asp)$_{ox}$ was followed on a 96 well plate during 40 minutes (25° C.) after incubation in PBS with peptide (25 µM) as listed in the accompanying table, or with 2 mM Dithiothreitol (DTT). Reduction was measured as a function of increase in fluorescence read at 530 nm after excitation at 494 nm, using a CytoFluor® multiplate reader (Applied Biosystems). tabe Example 2: Determination of the Activation of Cells Antigen specific NKT cells as obtained by the peptides of the present invention are capable to drive antigen presenting cells into apoptosis. To evaluate the activation and prevent eventual over-activation of the cytolytic cells which would drive them themselves in apoptosis, the phosphorylation status of Akt and Shp allows to draw a correlation between activation of a cell (capable of apoptosis) and over-activation of a cell (self-apoptosis).

Example 3: Polymerization of Human Recombinant CD1d

Human recombinant CD1d (300 ng) is incubated in Hepes buffer with 50 µM of a peptide with CD1d binding motif and redox motif for 15 minutes at 68° C. Fifty µM of DTT is used as a positive control under the same conditions. LDS sample buffer (7.5 µl; non-reducing) is then added to 15 µl of the peptide/CD1d mixture. The mixture is then submitted to non-reducing PAGE. After Coomassie Blue staining, protein bands are analyzed for the presence of monomeric, dimeric or multimeric recCD1d, as identified by the decreased migratory capacities into the gel.

Example 4: Control of Activation of NKT Cells Specific to Factor VIII by Immunization with a Peptide Containing a CD1d-Restricted T Cell Epitope and a Thioreductase Motif in Flanking Residues 4 groups of BALB/c Factor VIII KO mice are immunized 4 times at 1 week interval with 50 µg of a peptide, which contains a CD1d-restricted NKT cell. The different peptides which are used are:

```
                              [SEQ ID NO: 73]
GG FTNMFATWSPSK

[SEQ ID NO: 74]
CGHC GG FTNMFATWSPSK

[SEQ ID NO: 75]
HCGHC GG FTNMFATWSPSK

[SEQ ID NO: 76]
WCGHC GG FTNMFATWSPSK
```

Human factor VIII is then injected by the subcutaneous route using 10 IU per injection on 5 occasions separated by one week. Ten days after the last immunization the mice are sacrificed and spleen NKT cells are prepared by magnetic cell sorting. Such cells are stimulated twice with the immunizing peptide and FVIII in vitro before assessing their activation state as measured by the production of IL-4 and IFN-gamma. A control group is treated according to the same protocol but do not receive any peptide vaccination.

The reduction of IL-4 and IFN-gamma production by Factor VIII specific NKT obtained from mice immunized with the different peptides as compared to the control group is measured.

Example 5 Suppression of Anti-Ad5 IgG Antibody Response by Immunization with a Peptide Containing a CD1d-Restricted NKT Cell Epitope and a Thioreductase Motif Different groups of C57BL/6 mice (n=6) are immunized by four subcutaneous injections of 50 µg of a peptide in alum carried out at one-week interval.
The different peptides which are used are:

```
                              [SEQ ID NO: 77]
GG FIGLMYY

[SEQ ID NO: 78]
CHGC GG FIGLMYY

[SEQ ID NO: 79]
HCHGC GG FIGLMYY

[SEQ ID NO: 80]
WCHGC GG FIGLMYY
```

These peptides contain a CD1d-restricted NKT cell epitope of hexon protein of adenovirus (Ad5). A control group (n=6) of mice receives physiological serum in alum instead of peptide.

All mice then receive 2 injections of $10^9$ Ad5 viral particles by the IV route, separated by 1 week. Ten days after the last Ad5 injection, mice are bled and the concentration of total IgG antibodies to Ad5 particles is measured in a direct binding ELISA. Briefly, Ad5 viral particles are insolubilized on polystyrene plates, followed by washing and incubation with a dilution of mouse serum. After a second washing, the binding of mouse anti-Ad5 antibodies is detected by addition of a goat antiserum to mouse IgG.

Example 6: Induction of Apoptosis of Tumor Cells by CD4+ NKT Cells Elicited by Mouse Immunization with a Peptide Encompassing a CD1d Restricted NKT Epitope Containing a Thioreductase Motif Different groups of C57BL/6 mice (n=6) are immunized by four subcutaneous injections of 50 µg of peptide in alum carried out at one-week interval.
The different peptides which are used are:

```
                              [SEQ ID NO: 81]
GG FDKLPGF

[SEQ ID NO: 82]
CGHC GG FDKLPGF

[SEQ ID NO: 83]
HCGHC GG FDKLPGF

[SEQ ID NO: 84]
WCGHC GG FDKLPGF
```

Such peptides contain a CD1d-restricted NKT cell epitope derived from ovalbumin. A control group (n=6) of mice received physiological serum in alum instead of peptide. Ten days after the last immunization the mice are sacrificed and spleen CD4+ T cells are prepared by magnetic cell sorting. Such cells are stimulated twice with the immunizing peptide in vitro before assessing their activation state as measured by the production of IL-4 and IFN-gamma. CD4+ NKT cell lines are then assayed in vitro for their capacity to kill EG7 tumor cells. EG7 tumor cells (H-2b) are derived from a thymoma transduced with an ova construct. A CD1d restricted ova epitope is presented by such cells, which is known to be insufficient to trigger NKT activation and tumor cell killing. EG7 cells are labelled at membrane level with 1 µM DiOC18 (3,3'dioctadecycloxacarbocyanine perchlorate from Invitrogen). EG7 cells (1×10⁵ per well) are then cultured for 18 hat 37° C. in the presence of NKT cell lines at ratios of 1/1 to 1/5 (EG7 cells versus NKT cells). The NKT cell lines had first been stimulated for 4 h in vitro with antigen-presenting cells loaded with the respective peptide shown above. After 18 h, cells are harvested and stained for Annexin V and 7-AAD following manufacturer's instructions (Apoptosis Detection kit; BD Biosciences) and analysed on a FACSCantoll flow cytometer (BD Biosciences).

Example 7: Use of Tetramers of CD1d Molecules for the Detection of MOG-Specific CD4+ NKT Lymphocytes Multiple sclerosis is a chronic demyelination disease wherein CD4+ NKT cells towards auto antigens such as the myelin oligodendrocytic glycoprotein (MOG) are likely to play a key role. Its experimental equivalent, EAE (experimental autoimmune encephalomyelitis) mimic most of human disease hallmarks and is used to understand pathogenetic mechanisms and delineate new treatments. Enumerating MOG-specific CD4+ NKT cells could therefore be predictive of disease outcome. A CD1d binding epitope is identified in the mouse MOG protein by combination of algorithms and functional assay as described above, corresponding to sequence 200 to 206. CD4+ NKT cells are prepared from the spleen of C57BL/6 mice in which EAE has been induced. CD4(−) cells are first removed from the spleen cell suspension using magnetic beads. Tetramers of CD1d molecules (H-2b) are made as known in the art, including a fluorescent label such as phicoerythrin. A synthetic peptide is produced, which encompasses a CD1d-restricted MOG NKT cell epitope.

The peptides that are used are:

```
                                  [SEQ ID NO: 85]
GG FLRVPCWKI

[SEQ ID NO: 86]
CGPC GG FLRVPCWKI

[SEQ ID NO: 87]
HCGPC GG FLRVPCWKI

[SEQ ID NO: 88]
WCGPC GG FLRVPCWKI
```

Tetramers are loaded with peptide overnight at room temperature. Loaded tetramers are then washed and incubated with CD4+ T cells for 2 h at 37° C. The suspension is then read with a fluorescence-activated cell sorting system and the proportion of NKT cells specific to the MOG peptide is evaluated.

Example 8: Direct Killing of a H-2b Tumor Cell (R113) by NKT Cells Elicited with a CD1d-Restricted NKT Cell Epitope Derived from Anaplastic Lymphoma Kinase (ALK)

The anaplastic lymphoma kinase is a transmembrane receptor tyrosine kinase that is expressed on many cells during ontogeny, but only on tumors of ectodermal origin in adult life. It is therefore considered as an oncogen directly related to all tumors of ectodermal origin as shown in both animal models and human tumors. For example, up to 60% of human breast cancers express ALK. ALK+tumor cell lines of mouse origin are available and can be used to evaluate whether ALK-specific cytolytic NKT cells of the invention are able to kill tumor cells. NKT cells (C57BL/6, H-2b background) obtained from the spleen of naive mice are stimulated four times with autologous dendritic cells loaded with a CD1d-restricted NKT cell epitope of ALK, to which a thioreductase motif is added.

The peptides that are used are

```
                                   [SEQ ID NO: 89]
GG WLQIVTWWGPGS

[SEQ ID NO: 90]
CHGC GG WLQIVTWWGPGS

[SEQ ID NO: 91]
HCHGC GG WLQIVTWWGPGS

[SEQ ID NO: 92]
WCHGC GG WLQIVTWWGPGS
```

As NKT cells have per se a cytolytic activity, we included cells which are stimulated in parallel experiments by exposure to the same CD1d-restricted NKT epitope in natural sequence, without thioredox motif. Ten days after the last stimulation, NKT cells are washed and added to cell culture microplates containing 10⁴ R113 tum or cells at a 2 to 1 ratio (CD4 to tumor cells). R113 is a tumor B cell line obtained from C57BL/6 mice, which constitutively expresses ALK. After 20 h of co-culture, RI 13 tumor cells are evaluated for Annexin V binding used as marker of cell apoptosis.

In a second experiment, naive NKT cells from an alternative genetic background (BALB/c mice, H-2d background) are obtained from the spleen of naive mice and are stimulated four times with autologous dendritic cells loaded with the different peptides. Co-culture with a BALB/c-derived ALK+tumor cell line (VAC) is carried out as described above. Apoptosis of tumor cells is measured by evaluating Annexin-V binding by FACS.

Example 9: Prevention of EAE by Pre-Immunization with a Peptide Containing a CD1d Binding and a Thioreductase Motif EAE (experimental autoimmune encephalomyelitis) is a model disease in which central nervous system demyelination occurs and which is considered as the experimental equivalent of multiple sclerosis. A small number of autoantigens are considered to be implicated in the elicitation and maintenance of disease, among which the MOG (myelin oligodendrocytic glycoprotein). Disease can be elicited in the C57BL/6 mice by MOG immunization, using a CD1d binding peptide epitope encompassing MOG amino acids 35-55. MOG contains a sequence which binds to CD1d and activates NKT cells.

Peptides which are used are:

```
                                   [SEQ ID NO: 85]
GG FLRVPCWKI

[SEQ ID NO: 86]
CHGC GGFLRVPCWKI
```

```
                                                        [SEQ ID NO: 87]
            HCHGC GG FLRVPCWKI

[SEQ ID NO: 88]
            WCHGC GG FLRVPCWKI
```

Groups of C57BL/6 mice are immunized four times subcutaneously (50 μg) with peptide of SEQ ID NO: 86, 87 or 88 or, as a control, with peptide in natural sequence. Ten days after the last immunization, all mice, including a group of naive, non-immunized animals, are induced into disease by subcutaneous injection of 100 μg MOG 35-55 peptide/ 400 μg *Mycobacterium butyricum* in CFA and ip injection of 300 ng *Bortetella pertussis* in NaCl. At day +2, a second injection of *B. pertussis* is given. Signs of EAE are followed over time.

Example 10: Prevention and Suppression of Spontaneous Insulin-Dependent Diabetes with GAD65 Derived Peptides Non-obese diabetes (NOD) mice constitute a suitable animal model for spontaneous insulin-dependent diabetes. In such animals, as in human beings, an early immune response to the autoantigen glutamic acid decarboxylase (GAD65) is observed at a time at which insulitis can be seen, from which the response extends by intramolecular and intermolecular spreading. Inducing tolerance to GAD65 by administration of the protein to neonates prevents the onset of diabetes. GAD65 contains amino acid sequences with the capacity to bind to CD1d.

Peptides which are used are:

[SEQ ID NO: 93]
GG HTNVCFWFV

[SEQ ID NO: 94]
CHGC GG HTNVCFWFV

-continued

[SEQ ID NO: 95]
HCHGC GG HTNVCFWFV

[SEQ ID NO: 96]
WCHGC GG HTNVCFWFV

Female NOD mice are immunized from the age of 4 weeks by 4 subcutaneous injections, and glycaemia is followed in each of these groups, by comparison to a non-immunized group.

Example 11: Prevention of Asthma Induced by Exposure to an Allergen, Der p 1

Allergens from the house dust mite, *D. pteronyssinus*, are frequently involved in allergic asthma. Der p I is the main allergen of *D. pteronyssinus*. The sequence of Der p I contains a CD1d binding motif corresponding to amino acid sequence 38 to 44.

Peptides which are used are:

[SEQ ID NO: 97]
GG FSGVAATES

[SEQ ID NO: 98]
CGPC GG FSGVAATES

[SEQ ID NO: 99]
HCGPC GG FSGVAATES

[SEQ ID NO: 100]
WCGPC GG FSGVAATES

Allergic asthma can be induced in BALB/c mice by nasal instillations of 100 μg Der p 1 administered on 3 consecutive days. Asthma is characterized by bronchial hyper reactivity and attraction of eosinophil infiltrates into the lung. BALB/c mice are immunized by 4 injections of 50 μg of peptides of either SEQ ID NO: 98, 99 or 99 or peptide in natural sequence as a control. Der p1 is administered by nasal instillation 10 days after the last immunization. Airway reactivity to inhalation of methacholine lung infiltration with eosinophils is determined.

The invention claimed is:

1. An isolated fusion peptide of between 12 and 100 amino acids comprising
   (i) a first peptide of an antigen comprising the [FWYH]-X(2)-[VILM]-X(2)-[FWYH] (SEQ ID NO: 61) first sequence motif, wherein the antigen is myelin oligodendrocyte glycoprotein (MOG), and
   (ii) a [HW]-X(0,2)-C-X(2)-C ((SEQ ID NO: 7), (SEQ ID NO: 8), (SEQ ID NO: 9)) or C-X(2)-C-X(0,2)-[HW] ((SEQ ID NO: 10), (SEQ ID NO: 11), (SEQ ID NO: 12)) redox motif sequence, which is immediately adjacent or separated by at most 7 amino acids from said first sequence motif, wherein the redox motif sequence is located N terminally from the first sequence motif within the fusion peptide.

2. The fusion peptide of claim 1, wherein said fusion peptide has a length of between 12 and 50 amino acids.

3. The fusion peptide of claim 1, wherein the redox motif sequence is [HW]-C-X(2)-C (SEQ ID NO: 7) or C-X(2)-C-[HW] (SEQ ID NO: 10).

4. The fusion peptide of claim 1, wherein the redox motif sequence is H-C-X(2)-C (SEQ ID NO: 48) or C-X(2)-C-H (SEQ ID NO: 42).

5. The fusion peptide of claim 1, wherein said first peptide comprises the amino acid sequence of FLRVPCWKI (SEQ ID NO: 103).

6. The fusion peptide of claim 1, wherein said fusion peptide comprises the sequence of HCGPCGGFLRVPCWKI (SEQ ID NO: 87), WCGPCGGFLRVPCWKI (SEQ ID NO: 88), HCHGCGGFLRVPCWKI (SEQ ID NO: 105), or WCHGC GG FLRVPCWKI (SEQ ID NO: 106).

7. A method for preparing a peptide comprising the step of:
   identifying within an antigen a sequence comprising the [FWYH]-X(2)-[VILM]-X(2)-[FWYH] (SEQ ID NO: 61) first sequence motif, wherein the antigen is myelin oligodendrocyte glycoprotein (MOG); and
   preparing a peptide of between 12 and 100 amino comprising the first sequence motif and immediately adjacent or separated by at most 7 amino acids therefrom a [HW]-X(0,2)-C-X(2)-C ((SEQ ID NO: 7), (SEQ ID NO: 8), (SEQ ID NO: 9)) or C-X(2)-C-X(0,2)-[HW] ((SEQ ID NO: 10), (SEQ ID NO: 11), (SEQ ID NO: 12)) redox motif sequence, wherein the redox motif sequence is located N terminally from the first sequence motif within the fusion peptide.

8. The fusion peptide of claim 1, wherein the redox motif is [HW]-X(0,2)-C-X(2)-C ((SEQ ID NO: 7), (SEQ ID NO: 8), (SEQ ID NO: 9)).

9. The fusion peptide of claim 1, wherein the redox motif is [HW]-C-X(2)-C (SEQ ID NO: 7).

10. The fusion peptide of claim 1, wherein the redox motif is H-C-X(2)-C (SEQ ID NO: 48).

11. The fusion peptide of claim 1, wherein the first sequence motif is [FWY]-X(2)-[VILM]-X(2)-[FWY] (SEQ ID NO: 63).

12. The fusion peptide of claim 11, wherein the redox motif is [HW]-X(0,2)-C-X(2)-C ((SEQ ID NO: 7), (SEQ ID NO: 8), (SEQ ID NO: 9)).

13. The fusion peptide of claim 11, wherein the redox motif is [HW]-C-X(2)-C (SEQ ID NO: 7).

14. The fusion peptide of claim 11, wherein the redox motif is H-C-X(2)-C (SEQ ID NO: 48).

15. The fusion peptide of claim 5, wherein the redox motif is [HW]-X(0,2)-C-X(2)-C ((SEQ ID NO: 7), (SEQ ID NO: 8), (SEQ ID NO: 9)).

16. The fusion peptide of claim 5, wherein the redox motif is [HW]-C-X(2)-C (SEQ ID NO: 7).

17. The fusion peptide of claim 5, wherein the redox motif is H-C-X(2)-C (SEQ ID NO: 48).

18. An isolated fusion peptide of between 12 and 100 amino acids comprising
   (i) a first peptide of an antigen comprising the [FWYH]-X(2)-[VILM]-X(2)-[FWYH] (SEQ ID NO: 61) first sequence motif, wherein the antigen is myelin oligodendrocyte glycoprotein (MOG), and
   (ii) a [HW]-C-X(2)-C (SEQ ID NO: 7) or C-X(2)-C-[HW] (SEQ ID NO: 10) redox motif sequence, which is immediately adjacent or separated by at most 7 amino acids from said first sequence motif, wherein the redox motif sequence is located C terminally from the first sequence motif within the fusion peptide.

19. The fusion peptide of claim 5, wherein the redox motif is H-C-X(2)-C (SEQ ID NO: 48) or C-X(2)-C-H (SEQ ID NO: 42).

* * * * *

SEQUENCE LISTING

<160> NUMBER OF SEQ ID NOS: 106

<210> SEQ ID NO 1
<211> LENGTH: 5
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (1)..(1)
<223> OTHER INFORMATION: Xaa is His or Trp
<220> FEATURE:
<221> NAME/KEY: MISC_FEATURE
<222> LOCATION: (3)..(4)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa is Cys, Ser or Thr

<400> SEQUENCE: 1

Xaa Cys Xaa Xaa Xaa
1 5

```
<210> SEQ ID NO 2
<211> LENGTH: 6
<212> TYPE: PRT
<213> ORGANISM: Artificial Sequence
<220> FEATURE:
<223> OTHER INFORMATION: redox motif
<220> FEATURE:
<221> NAME/KEY: misc
<222> LOCATION: (1)..(1)
<223> OTHER INFORMATION: Xaa is His or Trp
<220> FEATURE:
<221> NAME/KEY: misc
<222> LOCATION: (2)..(2)
<223> OTHER INFORMATION: Xaa can be any amino acid
<220> FEATURE:
<221> NAME/KEY: misc
<222> LOCATION: (4)..(5)
<223> OTHER INFORMATION: Xaa can be any amino acid
<220> FEATURE:
<221> NAME/KEY: misc
<222> LOCATION: (6)..(6)
<223> OTHER INFORMATION: Xaa is Cys, Ser or Thr

<400> SEQUENCE: 2

Xaa Xaa Cys Xaa Xaa Xaa
1               5

<210> SEQ ID NO 3
<211> LENGTH: 7
<212> TYPE: PRT
<213> ORGANISM: Artificial Sequence
<220> FEATURE:
<223> OTHER INFORMATION: redox motif
<220> FEATURE:
<221> NAME/KEY: misc
<222> LOCATION: (1)..(1)
<223> OTHER INFORMATION: Xaa is His or Trp
<220> FEATURE:
<221> NAME/KEY: misc
<222> LOCATION: (2)..(3)
<223> OTHER INFORMATION: Xaa can be any amino acid
<220> FEATURE:
<221> NAME/KEY: misc
<222> LOCATION: (5)..(6)
<223> OTHER INFORMATION: Xaa can be any amino acid
<220> FEATURE:
<221> NAME/KEY: misc
<222> LOCATION: (7)..(7)
<223> OTHER INFORMATION: Xaa is Cys, Ser or Thr

<400> SEQUENCE: 3

Xaa Xaa Xaa Cys Xaa Xaa Xaa
1               5

<210> SEQ ID NO 4
<211> LENGTH: 5
<212> TYPE: PRT
<213> ORGANISM: Artificial Sequence
<220> FEATURE:
<223> OTHER INFORMATION: redox motif
<220> FEATURE:
<221> NAME/KEY: misc
<222> LOCATION: (1)..(1)
<223> OTHER INFORMATION: Xaa is Cys, Ser or Thr
<220> FEATURE:
<221> NAME/KEY: misc
<222> LOCATION: (2)..(3)
<223> OTHER INFORMATION: Xaa can be any amino acid
<220> FEATURE:
<221> NAME/KEY: misc
<222> LOCATION: (5)..(5)
<223> OTHER INFORMATION: Xaa is His or Trp

<400> SEQUENCE: 4
```

```
Xaa Xaa Xaa Cys Xaa
1               5

<210> SEQ ID NO 5
<211> LENGTH: 6
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (1)..(1)
<223> OTHER INFORMATION: Xaa is Cys, Ser or Thr
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is His or Trp

<400> SEQUENCE: 5

Xaa Xaa Xaa Cys Xaa Xaa
1               5

<210> SEQ ID NO 6
<211> LENGTH: 7
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (1)..(1)
<223> OTHER INFORMATION: Xaa is Cys, Ser or Thr
<220> FEATURE:
<221> NAME/KEY: MISC_FEATURE
<222> LOCATION: (2)..(3)
<223> OTHER INFORMATION: Xaa  can be any amino acid
<220> FEATURE:
<221> NAME/KEY: MISC_FEATURE
<222> LOCATION: (5)..(6)
<223> OTHER INFORMATION: Xaa  can be any amino acid
<220> FEATURE:
<221> NAME/KEY: MISC_FEATURE
<222> LOCATION: (7)..(7)
<223> OTHER INFORMATION: Xaa is His or Trp

<400> SEQUENCE: 6

Xaa Xaa Xaa Cys Xaa Xaa Xaa
1               5

<210> SEQ ID NO 7
<211> LENGTH: 5
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (1)..(1)
<223> OTHER INFORMATION: Xaa is His or Trp
<220> FEATURE:
<221> NAME/KEY: MISC_FEATURE
<222> LOCATION: (3)..(4)
<223> OTHER INFORMATION: Xaa can be any amino acid

<400> SEQUENCE: 7
```

```
Xaa Cys Xaa Xaa Cys
1               5
```

```
<210> SEQ ID NO 8
<211> LENGTH: 6
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (1)..(1)
<223> OTHER INFORMATION: Xaa is His or Trp
<220> FEATURE:
<221> NAME/KEY: MISC_FEATURE
<222> LOCATION: (2)..(2)
<223> OTHER INFORMATION: Xaa  can be any amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(6)
<223> OTHER INFORMATION: Xaa  can be any amino acid

<400> SEQUENCE: 8

Xaa Xaa Cys Xaa Xaa Cys
1               5
```

```
<210> SEQ ID NO 9
<211> LENGTH: 7
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (1)..(1)
<223> OTHER INFORMATION: Xaa is His or Trp
<220> FEATURE:
<221> NAME/KEY: MISC_FEATURE
<222> LOCATION: (2)..(3)
<223> OTHER INFORMATION: Xaa  can be any amino acid
<220> FEATURE:
<221> NAME/KEY: MISC_FEATURE
<222> LOCATION: (5)..(6)
<223> OTHER INFORMATION: Xaa  can be any amino acid

<400> SEQUENCE: 9

Xaa Xaa Xaa Cys Xaa Xaa Cys
1               5
```

```
<210> SEQ ID NO 10
<211> LENGTH: 5
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa is His or Trp

<400> SEQUENCE: 10

Cys Xaa Xaa Cys Xaa
1               5
```

```
<210> SEQ ID NO 11
<211> LENGTH: 6
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa can be any amino acid
<220> FEATURE:
<221> NAME/KEY: MISC_FEATURE
<222> LOCATION: (6)..(6)
<223> OTHER INFORMATION: Xaa is His or Trp

<400> SEQUENCE: 11

Cys Xaa Xaa Cys Xaa Xaa
1               5

<210> SEQ ID NO 12
<211> LENGTH: 7
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (5)..(6)
<223> OTHER INFORMATION: Xaa can be any amino acid
<220> FEATURE:
<221> NAME/KEY: MISC_FEATURE
<222> LOCATION: (7)..(7)
<223> OTHER INFORMATION: Xaa is His or Trp

<400> SEQUENCE: 12

Cys Xaa Xaa Cys Xaa Xaa Xaa
1               5

<210> SEQ ID NO 13
<211> LENGTH: 4
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any amino acid

<400> SEQUENCE: 13

Cys Xaa Xaa Cys
1

<210> SEQ ID NO 14
<211> LENGTH: 4
<212> TYPE: PRT
<213> ORGANISM: Artificial Sequence
<220> FEATURE:
<223> OTHER INFORMATION: redox motif
<220> FEATURE:
<221> NAME/KEY: misc
<222> LOCATION: (2)..(3)
<223> OTHER INFORMATION: Xaa can be any amino acid
```

```
<400> SEQUENCE: 14

Cys Xaa Xaa Ser
1

<210> SEQ ID NO 15
<211> LENGTH: 4
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any amino acid

<400> SEQUENCE: 15

Cys Xaa Xaa Thr
1

<210> SEQ ID NO 16
<211> LENGTH: 4
<212> TYPE: PRT
<213> ORGANISM: Artificial Sequence
<220> FEATURE:
<223> OTHER INFORMATION: redox motif
<220> FEATURE:
<221> NAME/KEY: misc
<222> LOCATION: (2)..(3)
<223> OTHER INFORMATION: Xaa can be any amino acid

<400> SEQUENCE: 16

Ser Xaa Xaa Cys
1

<210> SEQ ID NO 17
<211> LENGTH: 4
<212> TYPE: PRT
<213> ORGANISM: Artificial Sequence
<220> FEATURE:
<223> OTHER INFORMATION: redox motif
<220> FEATURE:
<221> NAME/KEY: misc
<222> LOCATION: (2)..(3)
<223> OTHER INFORMATION: Xaa can be any amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 17

Thr Cys Cys Xaa
1

<210> SEQ ID NO 18
<211> LENGTH: 5
<212> TYPE: PRT
<213> ORGANISM: Artificial Sequence
<220> FEATURE:
<223> OTHER INFORMATION: H-C-X(2)-S
<220> FEATURE:
<221> NAME/KEY: misc_feature
<222> LOCATION: (3)..(4)
<223> OTHER INFORMATION: Xaa can be any naturally occurring amino acid

<400> SEQUENCE: 18

His Cys Xaa Xaa Ser
1               5

<210> SEQ ID NO 19
```

```
<211> LENGTH: 6
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(2)
<223> OTHER INFORMATION: Xaa can be any amino acid
<220> FEATURE:
<221> NAME/KEY: MISC_FEATURE
<222> LOCATION: (4)..(5)
<223> OTHER INFORMATION: Xaa can be any amino acid

<400> SEQUENCE: 19

His Xaa Cys Xaa Xaa Ser
1               5

<210> SEQ ID NO 20
<211> LENGTH: 7
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (5)..(6)
<223> OTHER INFORMATION: Xaa can be any amino acid

<400> SEQUENCE: 20

His Xaa Xaa Cys Xaa Xaa Ser
1               5

<210> SEQ ID NO 21
<211> LENGTH: 5
<212> TYPE: PRT
<213> ORGANISM: Artificial Sequence
<220> FEATURE:
<223> OTHER INFORMATION: redox motif
<220> FEATURE:
<221> NAME/KEY: misc
<222> LOCATION: (3)..(4)
<223> OTHER INFORMATION: Xaa can be any amino acid

<400> SEQUENCE: 21

Trp Cys Xaa Xaa Ser
1               5

<210> SEQ ID NO 22
<211> LENGTH: 6
<212> TYPE: PRT
<213> ORGANISM: Artificial Sequence
<220> FEATURE:
<223> OTHER INFORMATION: redox motif
<220> FEATURE:
<221> NAME/KEY: misc
<222> LOCATION: (2)..(2)
<223> OTHER INFORMATION: Xaa can be any amino acid
<220> FEATURE:
<221> NAME/KEY: misc
<222> LOCATION: (4)..(5)
<223> OTHER INFORMATION: Xaa can be any amino acid

<400> SEQUENCE: 22

Trp Xaa Cys Xaa Xaa Ser
1               5
```

-continued

```
<210> SEQ ID NO 23
<211> LENGTH: 7
<212> TYPE: PRT
<213> ORGANISM: Artificial Sequence
<220> FEATURE:
<223> OTHER INFORMATION: redox motif
<220> FEATURE:
<221> NAME/KEY: misc
<222> LOCATION: (2)..(3)
<223> OTHER INFORMATION: Xaa can be any amino acid
<220> FEATURE:
<221> NAME/KEY: misc
<222> LOCATION: (5)..(6)
<223> OTHER INFORMATION: Xaa can be any amino acid

<400> SEQUENCE: 23

Trp Xaa Xaa Cys Xaa Xaa Ser
1               5

<210> SEQ ID NO 24
<211> LENGTH: 5
<212> TYPE: PRT
<213> ORGANISM: Artificial Sequence
<220> FEATURE:
<223> OTHER INFORMATION: redox motif
<220> FEATURE:
<221> NAME/KEY: misc
<222> LOCATION: (3)..(4)
<223> OTHER INFORMATION: Xaa can be any amino acid

<400> SEQUENCE: 24

His Cys Xaa Xaa Thr
1               5

<210> SEQ ID NO 25
<211> LENGTH: 6
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(2)
<223> OTHER INFORMATION: Xaa can be any amino acid
<220> FEATURE:
<221> NAME/KEY: MISC_FEATURE
<222> LOCATION: (4)..(5)
<223> OTHER INFORMATION: Xaa can be any amino acid

<400> SEQUENCE: 25

His Xaa Cys Xaa Xaa Thr
1               5

<210> SEQ ID NO 26
<211> LENGTH: 7
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (5)..(6)
<223> OTHER INFORMATION: Xaa can be any amino acid

<400> SEQUENCE: 26

His Xaa Xaa Cys Xaa Xaa Thr
1               5
```

```
<210> SEQ ID NO 27
<211> LENGTH: 5
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (3)..(4)
<223> OTHER INFORMATION: Xaa can be any amino acid

<400> SEQUENCE: 27

Trp Cys Xaa Xaa Thr
1               5

<210> SEQ ID NO 28
<211> LENGTH: 6
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(2)
<223> OTHER INFORMATION: Xaa can be any amino acid
<220> FEATURE:
<221> NAME/KEY: MISC_FEATURE
<222> LOCATION: (4)..(5)
<223> OTHER INFORMATION: Xaa can be any amino acid

<400> SEQUENCE: 28

Trp Xaa Cys Xaa Xaa Thr
1               5

<210> SEQ ID NO 29
<211> LENGTH: 7
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (5)..(6)
<223> OTHER INFORMATION: Xaa can be any amino acid

<400> SEQUENCE: 29

Trp Xaa Xaa Cys Xaa Xaa Thr
1               5

<210> SEQ ID NO 30
<211> LENGTH: 5
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any amino acid

<400> SEQUENCE: 30

Ser Xaa Xaa Cys His
1               5

<210> SEQ ID NO 31
<211> LENGTH: 6
```

```
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa can be any amino acid

<400> SEQUENCE: 31

Ser Xaa Xaa Cys Xaa His
1               5

<210> SEQ ID NO 32
<211> LENGTH: 7
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (5)..(6)
<223> OTHER INFORMATION: Xaa can be any amino acid

<400> SEQUENCE: 32

Ser Xaa Xaa Cys Xaa Xaa His
1               5

<210> SEQ ID NO 33
<211> LENGTH: 5
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa  can be any amino acid

<400> SEQUENCE: 33

Ser Xaa Xaa Cys Trp
1               5

<210> SEQ ID NO 34
<211> LENGTH: 6
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa can be any amino acid

<400> SEQUENCE: 34

Ser Xaa Xaa Cys Xaa Trp
1               5

<210> SEQ ID NO 35
```

```
<211> LENGTH: 7
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (5)..(6)
<223> OTHER INFORMATION: Xaa can be any amino acid

<400> SEQUENCE: 35

Ser Xaa Xaa Cys Xaa Xaa Trp
1               5

<210> SEQ ID NO 36
<211> LENGTH: 5
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any amino acid

<400> SEQUENCE: 36

Thr Xaa Xaa Cys His
1               5

<210> SEQ ID NO 37
<211> LENGTH: 6
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa can be any amino acid

<400> SEQUENCE: 37

Thr Xaa Xaa Cys Xaa His
1               5

<210> SEQ ID NO 38
<211> LENGTH: 7
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (5)..(6)
<223> OTHER INFORMATION: Xaa can be any amino acid

<400> SEQUENCE: 38

Thr Xaa Xaa Cys Xaa Xaa His
1               5
```

```
<210> SEQ ID NO 39
<211> LENGTH: 5
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any amino acid

<400> SEQUENCE: 39

Thr Xaa Xaa Cys Trp
1               5

<210> SEQ ID NO 40
<211> LENGTH: 6
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa can be any amino acid

<400> SEQUENCE: 40

Thr Xaa Xaa Cys Xaa Trp
1               5

<210> SEQ ID NO 41
<211> LENGTH: 7
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (5)..(6)
<223> OTHER INFORMATION: Xaa can be any amino acid

<400> SEQUENCE: 41

Thr Xaa Xaa Cys Xaa Xaa Trp
1               5

<210> SEQ ID NO 42
<211> LENGTH: 5
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any amino acid

<400> SEQUENCE: 42

Cys Xaa Xaa Cys His
1               5

<210> SEQ ID NO 43
<211> LENGTH: 6
<212> TYPE: PRT
```

```
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa can be any amino acid

<400> SEQUENCE: 43

Cys Xaa Xaa Cys Xaa His
1               5

<210> SEQ ID NO 44
<211> LENGTH: 7
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (5)..(6)
<223> OTHER INFORMATION: Xaa can be any amino acid

<400> SEQUENCE: 44

Cys Xaa Xaa Cys Xaa Xaa His
1               5

<210> SEQ ID NO 45
<211> LENGTH: 5
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa  can be any amino acid

<400> SEQUENCE: 45

Cys Xaa Xaa Cys Trp
1               5

<210> SEQ ID NO 46
<211> LENGTH: 6
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa can be any amino acid

<400> SEQUENCE: 46

Cys Xaa Xaa Cys Xaa Trp
1               5

<210> SEQ ID NO 47
<211> LENGTH: 7
```

```
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (5)..(6)
<223> OTHER INFORMATION: Xaa can be any amino acid

<400> SEQUENCE: 47

Cys Xaa Xaa Cys Xaa Xaa Trp
1               5

<210> SEQ ID NO 48
<211> LENGTH: 5
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 48

His Cys Xaa Xaa Cys
1               5

<210> SEQ ID NO 49
<211> LENGTH: 6
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be any amino acid

<400> SEQUENCE: 49

His Xaa Cys Xaa Xaa Cys
1               5

<210> SEQ ID NO 50
<211> LENGTH: 7
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (5)..(6)
<223> OTHER INFORMATION: Xaa can be any amino acid
```

```
<400> SEQUENCE: 50

His Xaa Xaa Cys Xaa Xaa Cys
1               5

<210> SEQ ID NO 51
<211> LENGTH: 5
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 51

Trp Cys Xaa Xaa Cys
1               5

<210> SEQ ID NO 52
<211> LENGTH: 6
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(2)
<223> OTHER INFORMATION: Xaa can be any amino acid
<220> FEATURE:
<221> NAME/KEY: MISC_FEATURE
<222> LOCATION: (4)..(5)
<223> OTHER INFORMATION: Xaa can be any amino acid

<400> SEQUENCE: 52

Trp Xaa Cys Xaa Xaa Cys
1               5

<210> SEQ ID NO 53
<211> LENGTH: 7
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (5)..(6)
<223> OTHER INFORMATION: Xaa can be any amino acid

<400> SEQUENCE: 53

Trp Xaa Xaa Cys Xaa Xaa Cys
1               5

<210> SEQ ID NO 54
<211> LENGTH: 4
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (1)..(1)
```

```
<223> OTHER INFORMATION: Xaa is Cys, Ser or Thr
<220> FEATURE:
<221> NAME/KEY: MISC_FEATURE
<222> LOCATION: (2)..(3)
<223> OTHER INFORMATION: Xaa can be any amino acid

<400> SEQUENCE: 54

Xaa Xaa Xaa Cys
1

<210> SEQ ID NO 55
<211> LENGTH: 4
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (4)..(4)
<223> OTHER INFORMATION: Xaa is Cys, Ser or Thr

<400> SEQUENCE: 55

Cys Xaa Xaa Xaa
1

<210> SEQ ID NO 56
<211> LENGTH: 6
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (4)..(5)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is Cys, Ser or Thr

<400> SEQUENCE: 56

His Xaa Cys Xaa Xaa Xaa
1               5

<210> SEQ ID NO 57
<211> LENGTH: 6
<212> TYPE: PRT
<213> ORGANISM: Artificial Sequence
<220> FEATURE:
<223> OTHER INFORMATION: redox motif
<220> FEATURE:
<221> NAME/KEY: misc
<222> LOCATION: (1)..(1)
<223> OTHER INFORMATION: Xaa is Cys, Ser or Thr
<220> FEATURE:
<221> NAME/KEY: misc
<222> LOCATION: (2)..(3)
<223> OTHER INFORMATION: Xaa can be any amino acid
<220> FEATURE:
<221> NAME/KEY: misc
<222> LOCATION: (5)..(5)
<223> OTHER INFORMATION: Xaa can be any amino acid

<400> SEQUENCE: 57
```

Xaa Xaa Xaa Cys Xaa His
1               5

<210> SEQ ID NO 58
<211> LENGTH: 6
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (1)..(1)
<223> OTHER INFORMATION: Xaa is Cys, Ser or Thr
<220> FEATURE:
<221> NAME/KEY: MISC_FEATURE
<222> LOCATION: (2)..(2)
<223> OTHER INFORMATION: Xaa  can be any amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa  can be any amino acid

<400> SEQUENCE: 58

Xaa Xaa Xaa Cys Xaa Trp
1               5

<210> SEQ ID NO 59
<211> LENGTH: 6
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(2)
<223> OTHER INFORMATION: Xaa can be any amino acid
<220> FEATURE:
<221> NAME/KEY: MISC_FEATURE
<222> LOCATION: (4)..(5)
<223> OTHER INFORMATION: Xaa can be any amino acid
<220> FEATURE:
<221> NAME/KEY: MISC_FEATURE
<222> LOCATION: (6)..(6)
<223> OTHER INFORMATION: Xaa is Cys, Ser or Thr

<400> SEQUENCE: 59

Trp Xaa Cys Xaa Xaa Xaa
1               5

<210> SEQ ID NO 60
<211> LENGTH: 7
<212> TYPE: PRT
<213> ORGANISM: Artificial Sequence
<220> FEATURE:
<223> OTHER INFORMATION: CD1d binding motif
<220> FEATURE:
<221> NAME/KEY: misc
<222> LOCATION: (1)..(1)
<223> OTHER INFORMATION: Xaa is Phe, Trp, Tyr, His or Thr
<220> FEATURE:
<221> NAME/KEY: misc
<222> LOCATION: (2)..(3)
<223> OTHER INFORMATION: Xaa can be any amino acid
<220> FEATURE:
<221> NAME/KEY: misc
<222> LOCATION: (4)..(4)
<223> OTHER INFORMATION: Xaa is Val, Ile, Leu or Met
<220> FEATURE:
<221> NAME/KEY: misc
<222> LOCATION: (5)..(6)

<223> OTHER INFORMATION: Xaa can be any amino acid
<220> FEATURE:
<221> NAME/KEY: misc
<222> LOCATION: (7)..(7)
<223> OTHER INFORMATION: Xaa is Phe, Trp, Tyr, His or Thr

<400> SEQUENCE: 60

Xaa Xaa Xaa Xaa Xaa Xaa Xaa
1               5

<210> SEQ ID NO 61
<211> LENGTH: 7
<212> TYPE: PRT
<213> ORGANISM: Artificial Sequence
<220> FEATURE:
<223> OTHER INFORMATION: CD1d binding motif
<220> FEATURE:
<221> NAME/KEY: MISC_FEATURE
<222> LOCATION: (1)..(1)
<223> OTHER INFORMATION: Xaa is Phe, Trp, Tyr or His
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (4)..(4)
<223> OTHER INFORMATION: Xaa is Val. Ile, Leu or Met
<220> FEATURE:
<221> NAME/KEY: MISC_FEATURE
<222> LOCATION: (5)..(6)
<223> OTHER INFORMATION: Xaa can be any amino acid
<220> FEATURE:
<221> NAME/KEY: MISC_FEATURE
<222> LOCATION: (7)..(7)
<223> OTHER INFORMATION: Xaa is Phe, Trp, Tyr or His

<400> SEQUENCE: 61

Xaa Xaa Xaa Xaa Xaa Xaa Xaa
1               5

<210> SEQ ID NO 62
<211> LENGTH: 7
<212> TYPE: PRT
<213> ORGANISM: Artificial Sequence
<220> FEATURE:
<223> OTHER INFORMATION: CD1d binding motif
<220> FEATURE:
<221> NAME/KEY: MISC_FEATURE
<222> LOCATION: (1)..(1)
<223> OTHER INFORMATION: Xaa is Phe, Trp Tyr or Thr
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (4)..(4)
<223> OTHER INFORMATION: Xaa is Val, Ile, Leu or Met
<220> FEATURE:
<221> NAME/KEY: MISC_FEATURE
<222> LOCATION: (5)..(6)
<223> OTHER INFORMATION: Xaa can be any amino acid
<220> FEATURE:
<221> NAME/KEY: MISC_FEATURE
<222> LOCATION: (7)..(7)
<223> OTHER INFORMATION: Xaa is Phe, Trp Tyr or Thr

<400> SEQUENCE: 62

Xaa Xaa Xaa Xaa Xaa Xaa Xaa
1               5

<210> SEQ ID NO 63

```
<211> LENGTH: 7
<212> TYPE: PRT
<213> ORGANISM: Artificial Sequence
<220> FEATURE:
<223> OTHER INFORMATION: CD1d binding motif
<220> FEATURE:
<221> NAME/KEY: MISC_FEATURE
<222> LOCATION: (1)..(1)
<223> OTHER INFORMATION: Xaa is Phe, Trp or Tyr
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (4)..(4)
<223> OTHER INFORMATION: Xaa is Val, Ile, Leu or Met
<220> FEATURE:
<221> NAME/KEY: MISC_FEATURE
<222> LOCATION: (5)..(6)
<223> OTHER INFORMATION: Xaa can be any amino acid
<220> FEATURE:
<221> NAME/KEY: MISC_FEATURE
<222> LOCATION: (7)..(7)
<223> OTHER INFORMATION: Xaa is Phe, Trp or Tyr

<400> SEQUENCE: 63

Xaa Xaa Xaa Xaa Xaa Xaa Xaa
1               5

<210> SEQ ID NO 64
<211> LENGTH: 7
<212> TYPE: PRT
<213> ORGANISM: Artificial Sequence
<220> FEATURE:
<223> OTHER INFORMATION: CD1d binding motif
<220> FEATURE:
<221> NAME/KEY: MISC_FEATURE
<222> LOCATION: (1)..(1)
<223> OTHER INFORMATION: Xaa is Phe, Trp Tyr or His
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (4)..(4)
<223> OTHER INFORMATION: Xaa is Ile, Leu or Met
<220> FEATURE:
<221> NAME/KEY: MISC_FEATURE
<222> LOCATION: (5)..(6)
<223> OTHER INFORMATION: Xaa can be any amino acid
<220> FEATURE:
<221> NAME/KEY: MISC_FEATURE
<222> LOCATION: (7)..(7)
<223> OTHER INFORMATION: Xaa is Phe, Trp Tyr or His

<400> SEQUENCE: 64

Xaa Xaa Xaa Xaa Xaa Xaa Xaa
1               5

<210> SEQ ID NO 65
<211> LENGTH: 7
<212> TYPE: PRT
<213> ORGANISM: Artificial Sequence
<220> FEATURE:
<223> OTHER INFORMATION: CD1d binding motif
<220> FEATURE:
<221> NAME/KEY: MISC_FEATURE
<222> LOCATION: (1)..(1)
<223> OTHER INFORMATION: Xaa is Phe, Trp, Tyr His or Thr
<220> FEATURE:
<221> NAME/KEY: MISC_FEATURE
<222> LOCATION: (2)..(3)
<223> OTHER INFORMATION: Xaa can be any amino acid
```

```
<220> FEATURE:
<221> NAME/KEY: MISC_FEATURE
<222> LOCATION: (4)..(4)
<223> OTHER INFORMATION: Xaa is Ile, Leu or Met
<220> FEATURE:
<221> NAME/KEY: MISC_FEATURE
<222> LOCATION: (5)..(6)
<223> OTHER INFORMATION: Xaa can be any amino acid
<220> FEATURE:
<221> NAME/KEY: MISC_FEATURE
<222> LOCATION: (7)..(7)
<223> OTHER INFORMATION: Xaa is Phe, Trp, Tyr His or Thr

<400> SEQUENCE: 65

Xaa Xaa Xaa Xaa Xaa Xaa Xaa
1               5

<210> SEQ ID NO 66
<211> LENGTH: 7
<212> TYPE: PRT
<213> ORGANISM: Artificial Sequence
<220> FEATURE:
<223> OTHER INFORMATION: CD1d binding motif
<220> FEATURE:
<221> NAME/KEY: MISC_FEATURE
<222> LOCATION: (1)..(1)
<223> OTHER INFORMATION: Xaa is Phe, Trp or Tyr
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (4)..(4)
<223> OTHER INFORMATION: Xaa is Ile, Leu or Met
<220> FEATURE:
<221> NAME/KEY: MISC_FEATURE
<222> LOCATION: (5)..(6)
<223> OTHER INFORMATION: Xaa can be any amino acid
<220> FEATURE:
<221> NAME/KEY: MISC_FEATURE
<222> LOCATION: (7)..(7)
<223> OTHER INFORMATION: Xaa is Phe, Trp or Tyr

<400> SEQUENCE: 66

Xaa Xaa Xaa Xaa Xaa Xaa Xaa
1               5

<210> SEQ ID NO 67
<211> LENGTH: 6
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: Xaa is His or Trp
<220> FEATURE:
<221> NAME/KEY: MISC_FEATURE
<222> LOCATION: (3)..(4)
<223> OTHER INFORMATION: Xaa can be any amino acid
<220> FEATURE:
<221> NAME/KEY: MISC_FEATURE
<222> LOCATION: (6)..(6)
<223> OTHER INFORMATION: Xaa is His or Trp

<400> SEQUENCE: 67

Xaa Cys Xaa Xaa Cys Xaa
1               5

<210> SEQ ID NO 68
<211> LENGTH: 5
```

```
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (4)..(4)
<223> OTHER INFORMATION: Xaa can be any amino acid

<400> SEQUENCE: 68

His Cys His Xaa Cys
1               5

<210> SEQ ID NO 69
<211> LENGTH: 5
<212> TYPE: PRT
<213> ORGANISM: Artificial Sequence
<220> FEATURE:
<223> OTHER INFORMATION: peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be any amino acid

<400> SEQUENCE: 69

Trp Cys Trp Xaa Cys
1               5

<210> SEQ ID NO 70
<211> LENGTH: 6
<212> TYPE: PRT
<213> ORGANISM: Artificial Sequence
<220> FEATURE:
<223> OTHER INFORMATION: late endosome targeting signal
<220> FEATURE:
<221> NAME/KEY: MISC_FEATURE
<222> LOCATION: (1)..(1)
<223> OTHER INFORMATION: Xaa is Asp or Glu
<220> FEATURE:
<221> NAME/KEY: MISC_FEATURE
<222> LOCATION: (2)..(4)
<223> OTHER INFORMATION: Xaa can be any amino acid
<220> FEATURE:
<221> NAME/KEY: MISC_FEATURE
<222> LOCATION: (6)..(6)
<223> OTHER INFORMATION: Xaa is Ile or Leu

<400> SEQUENCE: 70

Xaa Xaa Xaa Xaa Leu Xaa
1               5

<210> SEQ ID NO 71
<211> LENGTH: 5
<212> TYPE: PRT
<213> ORGANISM: Artificial Sequence
<220> FEATURE:
<223> OTHER INFORMATION: late endosome targeting signal
<220> FEATURE:
<221> NAME/KEY: MISC_FEATURE
<222> LOCATION: (2)..(3)
<223> OTHER INFORMATION: Xaa can be any amino acid

<400> SEQUENCE: 71

Asp Xaa Xaa Leu Leu
1               5

<210> SEQ ID NO 72
```

```
<211> LENGTH: 4
<212> TYPE: PRT
<213> ORGANISM: Artificial Sequence
<220> FEATURE:
<223> OTHER INFORMATION: late endosome targeting sequence
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (4)..(4)
<223> OTHER INFORMATION: Xaa is Phe, Tyr or Trp

<400> SEQUENCE: 72

Tyr Xaa Xaa Xaa
1

<210> SEQ ID NO 73
<211> LENGTH: 14
<212> TYPE: PRT
<213> ORGANISM: Artificial Sequence
<220> FEATURE:
<223> OTHER INFORMATION: Factor VIII

<400> SEQUENCE: 73

Gly Gly Phe Thr Asn Met Phe Ala Thr Trp Ser Pro Ser Lys
1               5                   10

<210> SEQ ID NO 74
<211> LENGTH: 18
<212> TYPE: PRT
<213> ORGANISM: Artificial Sequence
<220> FEATURE:
<223> OTHER INFORMATION: factor VIII

<400> SEQUENCE: 74

Cys Gly His Cys Gly Gly Phe Thr Asn Met Phe Ala Thr Trp Ser Pro
1               5                   10                  15

Ser Lys

<210> SEQ ID NO 75
<211> LENGTH: 19
<212> TYPE: PRT
<213> ORGANISM: Artificial Sequence
<220> FEATURE:
<223> OTHER INFORMATION: Factor VIII

<400> SEQUENCE: 75

His Cys Gly His Cys Gly Gly Phe Thr Asn Met Phe Ala Thr Trp Ser
1               5                   10                  15

Pro Ser Lys

<210> SEQ ID NO 76
<211> LENGTH: 19
<212> TYPE: PRT
<213> ORGANISM: Artificial Sequence
<220> FEATURE:
<223> OTHER INFORMATION: Factor VIII

<400> SEQUENCE: 76

Trp Cys Gly His Cys Gly Gly Phe Thr Asn Met Phe Ala Thr Trp Ser
1               5                   10                  15

Pro Ser Lys

<210> SEQ ID NO 77
```

```
<211> LENGTH: 9
<212> TYPE: PRT
<213> ORGANISM: Artificial Sequence
<220> FEATURE:
<223> OTHER INFORMATION: hexon Ad5

<400> SEQUENCE: 77

Gly Gly Phe Ile Gly Leu Met Tyr Tyr
1               5

<210> SEQ ID NO 78
<211> LENGTH: 13
<212> TYPE: PRT
<213> ORGANISM: Artificial Sequence
<220> FEATURE:
<223> OTHER INFORMATION: Hexon Ad5

<400> SEQUENCE: 78

Cys His Gly Cys Gly Gly Phe Ile Gly Leu Met Tyr Tyr
1               5                   10

<210> SEQ ID NO 79
<211> LENGTH: 14
<212> TYPE: PRT
<213> ORGANISM: Artificial Sequence
<220> FEATURE:
<223> OTHER INFORMATION: Hexon Ad5

<400> SEQUENCE: 79

His Cys His Gly Cys Gly Gly Phe Ile Gly Leu Met Tyr Tyr
1               5                   10

<210> SEQ ID NO 80
<211> LENGTH: 14
<212> TYPE: PRT
<213> ORGANISM: Artificial Sequence
<220> FEATURE:
<223> OTHER INFORMATION: Hexon Ad5

<400> SEQUENCE: 80

Trp Cys His Gly Cys Gly Gly Phe Ile Gly Leu Met Tyr Tyr
1               5                   10

<210> SEQ ID NO 81
<211> LENGTH: 9
<212> TYPE: PRT
<213> ORGANISM: Artificial Sequence
<220> FEATURE:
<223> OTHER INFORMATION: ovalbumin

<400> SEQUENCE: 81

Gly Gly Phe Asp Lys Leu Pro Gly Phe
1               5

<210> SEQ ID NO 82
<211> LENGTH: 13
<212> TYPE: PRT
<213> ORGANISM: Artificial Sequence
<220> FEATURE:
<223> OTHER INFORMATION: ovalbumin

<400> SEQUENCE: 82

Cys Gly His Cys Gly Gly Phe Asp Lys Leu Pro Gly Phe
1               5                   10

<210> SEQ ID NO 83
<211> LENGTH: 14
```

```
<212> TYPE: PRT
<213> ORGANISM: Artificial Sequence
<220> FEATURE:
<223> OTHER INFORMATION: ovalbumin

<400> SEQUENCE: 83

His Cys Gly His Cys Gly Gly Phe Asp Lys Leu Pro Gly Phe
1               5                   10

<210> SEQ ID NO 84
<211> LENGTH: 14
<212> TYPE: PRT
<213> ORGANISM: Artificial Sequence
<220> FEATURE:
<223> OTHER INFORMATION: ovalbumin

<400> SEQUENCE: 84

Trp Cys Gly His Cys Gly Gly Phe Asp Lys Leu Pro Gly Phe
1               5                   10

<210> SEQ ID NO 85
<211> LENGTH: 11
<212> TYPE: PRT
<213> ORGANISM: Artificial Sequence
<220> FEATURE:
<223> OTHER INFORMATION: MOG

<400> SEQUENCE: 85

Gly Gly Phe Leu Arg Val Pro Cys Trp Lys Ile
1               5                   10

<210> SEQ ID NO 86
<211> LENGTH: 15
<212> TYPE: PRT
<213> ORGANISM: Artificial Sequence
<220> FEATURE:
<223> OTHER INFORMATION: MOG

<400> SEQUENCE: 86

Cys Gly Pro Cys Gly Gly Phe Leu Arg Val Pro Cys Trp Lys Ile
1               5                   10                  15

<210> SEQ ID NO 87
<211> LENGTH: 16
<212> TYPE: PRT
<213> ORGANISM: Artificial Sequence
<220> FEATURE:
<223> OTHER INFORMATION: MOG

<400> SEQUENCE: 87

His Cys Gly Pro Cys Gly Gly Phe Leu Arg Val Pro Cys Trp Lys Ile
1               5                   10                  15

<210> SEQ ID NO 88
<211> LENGTH: 16
<212> TYPE: PRT
<213> ORGANISM: Artificial Sequence
<220> FEATURE:
<223> OTHER INFORMATION: MOG

<400> SEQUENCE: 88

Trp Cys Gly Pro Cys Gly Gly Phe Leu Arg Val Pro Cys Trp Lys Ile
1               5                   10                  15

<210> SEQ ID NO 89
<211> LENGTH: 14
<212> TYPE: PRT
```

```
<213> ORGANISM: Artificial Sequence
<220> FEATURE:
<223> OTHER INFORMATION: ALK

<400> SEQUENCE: 89

Gly Gly Trp Leu Gln Ile Val Thr Trp Trp Gly Pro Gly Ser
1               5                   10

<210> SEQ ID NO 90
<211> LENGTH: 18
<212> TYPE: PRT
<213> ORGANISM: Artificial Sequence
<220> FEATURE:
<223> OTHER INFORMATION: ALK

<400> SEQUENCE: 90

Cys His Gly Cys Gly Gly Trp Leu Gln Ile Val Thr Trp Trp Gly Pro
1               5                   10                  15

Gly Ser

<210> SEQ ID NO 91
<211> LENGTH: 19
<212> TYPE: PRT
<213> ORGANISM: Artificial Sequence
<220> FEATURE:
<223> OTHER INFORMATION: ALK

<400> SEQUENCE: 91

His Cys His Gly Cys Gly Gly Trp Leu Gln Ile Val Thr Trp Trp Gly
1               5                   10                  15

Pro Gly Ser

<210> SEQ ID NO 92
<211> LENGTH: 19
<212> TYPE: PRT
<213> ORGANISM: Artificial Sequence
<220> FEATURE:
<223> OTHER INFORMATION: ALK

<400> SEQUENCE: 92

Trp Cys His Gly Cys Gly Gly Trp Leu Gln Ile Val Thr Trp Trp Gly
1               5                   10                  15

Pro Gly Ser

<210> SEQ ID NO 93
<211> LENGTH: 11
<212> TYPE: PRT
<213> ORGANISM: Artificial Sequence
<220> FEATURE:
<223> OTHER INFORMATION: Gad65

<400> SEQUENCE: 93

Gly Gly His Thr Asn Val Cys Phe Trp Phe Val
1               5                   10

<210> SEQ ID NO 94
<211> LENGTH: 15
<212> TYPE: PRT
<213> ORGANISM: Artificial Sequence
<220> FEATURE:
<223> OTHER INFORMATION: Gad65

<400> SEQUENCE: 94

Cys His Gly Cys Gly Gly His Thr Asn Val Cys Phe Trp Phe Val
1               5                   10                  15
```

```
<210> SEQ ID NO 95
<211> LENGTH: 16
<212> TYPE: PRT
<213> ORGANISM: Artificial Sequence
<220> FEATURE:
<223> OTHER INFORMATION: Gad65

<400> SEQUENCE: 95

His Cys His Gly Cys Gly Gly His Thr Asn Val Cys Phe Trp Phe Val
1               5                   10                  15

<210> SEQ ID NO 96
<211> LENGTH: 16
<212> TYPE: PRT
<213> ORGANISM: Artificial Sequence
<220> FEATURE:
<223> OTHER INFORMATION: Gad65

<400> SEQUENCE: 96

Trp Cys His Gly Cys Gly Gly His Thr Asn Val Cys Phe Trp Phe Val
1               5                   10                  15

<210> SEQ ID NO 97
<211> LENGTH: 11
<212> TYPE: PRT
<213> ORGANISM: Artificial Sequence
<220> FEATURE:
<223> OTHER INFORMATION: Derp1

<400> SEQUENCE: 97

Gly Gly Phe Ser Gly Val Ala Ala Thr Glu Ser
1               5                   10

<210> SEQ ID NO 98
<211> LENGTH: 15
<212> TYPE: PRT
<213> ORGANISM: Artificial Sequence
<220> FEATURE:
<223> OTHER INFORMATION: Derp1

<400> SEQUENCE: 98

Cys Gly Pro Cys Gly Gly Phe Ser Gly Val Ala Ala Thr Glu Ser
1               5                   10                  15

<210> SEQ ID NO 99
<211> LENGTH: 16
<212> TYPE: PRT
<213> ORGANISM: Artificial Sequence
<220> FEATURE:
<223> OTHER INFORMATION: Gad65

<400> SEQUENCE: 99

His Cys Gly Pro Cys Gly Gly Phe Ser Gly Val Ala Ala Thr Glu Ser
1               5                   10                  15

<210> SEQ ID NO 100
<211> LENGTH: 16
<212> TYPE: PRT
<213> ORGANISM: Artificial Sequence
<220> FEATURE:
<223> OTHER INFORMATION: Derp1

<400> SEQUENCE: 100

Trp Cys Gly Pro Cys Gly Gly Phe Ser Gly Val Ala Ala Thr Glu Ser
1               5                   10                  15
```

```
<210> SEQ ID NO 101
<211> LENGTH: 5
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (3)..(4)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa is Cys, Ser or Thr

<400> SEQUENCE: 101

His Cys Xaa Xaa Xaa
1               5

<210> SEQ ID NO 102
<211> LENGTH: 5
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (1)..(1)
<223> OTHER INFORMATION: Xaa is Cys, Ser or Thr
<220> FEATURE:
<221> NAME/KEY: MISC_FEATURE
<222> LOCATION: (2)..(3)
<223> OTHER INFORMATION: Xaa can be any amino acid

<400> SEQUENCE: 102

Xaa Xaa Xaa Cys His
1               5

<210> SEQ ID NO 103
<211> LENGTH: 9
<212> TYPE: PRT
<213> ORGANISM: Artificial Sequence
<220> FEATURE:
<223> OTHER INFORMATION: MOG

<400> SEQUENCE: 103

Phe Leu Arg Val Pro Cys Trp Lys Ile
1               5

<210> SEQ ID NO 104
<211> LENGTH: 15
<212> TYPE: PRT
<213> ORGANISM: Artificial Sequence
<220> FEATURE:
<223> OTHER INFORMATION: MOG

<400> SEQUENCE: 104

Cys His Gly Cys Gly Gly Phe Leu Arg Val Pro Cys Trp Lys Ile
1               5                   10                  15

<210> SEQ ID NO 105
<211> LENGTH: 16
<212> TYPE: PRT
<213> ORGANISM: Artificial Sequence
<220> FEATURE:
<223> OTHER INFORMATION: MOG

<400> SEQUENCE: 105

His Cys His Gly Cys Gly Gly Phe Leu Arg Val Pro Cys Trp Lys Ile
```

-continued

```
1               5                   10                  15

<210> SEQ ID NO 106
<211> LENGTH: 16
<212> TYPE: PRT
<213> ORGANISM: Artificial Sequence
<220> FEATURE:
<223> OTHER INFORMATION: MOG

<400> SEQUENCE: 106

Trp Cys His Gly Cys Gly Gly Phe Leu Arg Val Pro Cys Trp Lys Ile
1               5                   10                  15
```